United States Patent
Nair et al.

(10) Patent No.: US 11,565,046 B2
(45) Date of Patent: Jan. 31, 2023

(54) AUTO-INJECTOR

(71) Applicant: University of Cape Town, CapeTown (ZA)

(72) Inventors: Gokul Arjunan Nair, Cape Town (ZA); Michael Levin, Cape Town (ZA); Sudesh Sivarasu, Kenilworth (ZA)

(73) Assignee: UNIVERSITY OF CAPE TOWN, Cape Town (ZA)

( * ) Notice: Subject to any disclaimer, the term of this patent is extended or adjusted under 35 U.S.C. 154(b) by 580 days.

(21) Appl. No.: 16/493,553

(22) PCT Filed: Mar. 12, 2018

(86) PCT No.: PCT/IB2018/051623
§ 371 (c)(1),
(2) Date: Sep. 12, 2019

(87) PCT Pub. No.: WO2018/167640
PCT Pub. Date: Sep. 20, 2018

(65) Prior Publication Data
US 2020/0009323 A1    Jan. 9, 2020

(30) Foreign Application Priority Data
Mar. 13, 2017    (GB) .................................... 1703982

(51) Int. Cl.
*A61M 5/20*    (2006.01)
*A61M 5/24*    (2006.01)

(52) U.S. Cl.
CPC ............ *A61M 5/2033* (2013.01); *A61M 5/24* (2013.01); *A61M 2005/206* (2013.01); *A61M 2005/208* (2013.01); *A61M 2005/2013* (2013.01)

(58) Field of Classification Search
CPC ........ A61M 5/2033; A61M 5/24; A61M 5/20; A61M 2005/2013; A61M 2005/206; A61M 2005/208; A61M 2005/2073
See application file for complete search history.

(56) References Cited

U.S. PATENT DOCUMENTS 5,271,744 A * 12/1993 Kramer ................. A61M 5/326
                                                                    604/506
5,300,030 A    4/1994 Crossman
(Continued)

FOREIGN PATENT DOCUMENTS

| CA | 2586552 A1 | 6/1999 |
| EP | 2923714 A1 | 9/2015 |

(Continued)

OTHER PUBLICATIONS

International Search Report and Written Opinion for PCT/IB2018/051623 dated Jul. 17, 2018, 8 pages.
(Continued)

*Primary Examiner* — Tasnim Mehjabin Ahmed
(74) *Attorney, Agent, or Firm* — Myers Bigel, P.A.

(57) ABSTRACT

An auto-injector is provided which includes a housing with a syringe slidably received therein. The syringe has a barrel with a piston movable therein and a needle extending therefrom. The piston is releasably secured to one end of a plunger which is slidably secured within a body in the housing and is operable through a bias provided by a motive source. In use, the plunger moves under the bias from a loaded condition to a discharged condition to move the syringe so that the needle extends from a tip at an injection end of the housing and to slide the piston within the barrel to expel the contents of the syringe. The plunger is held in the loaded condition against the bias by a detent extending (Continued)

from the body and which can be selectively released by operation of an actuator when pressure is applied to the tip.

13 Claims, 17 Drawing Sheets

(56) References Cited

U.S. PATENT DOCUMENTS

| | | | |
|---|---|---|---|
| 2008/0051715 A1 | 2/2008 | Young et al. | |
| 2008/0228143 A1* | 9/2008 | Stamp | A61M 5/2033 604/157 |
| 2016/0067144 A1* | 3/2016 | Chang | A61M 5/1409 604/92 |

FOREIGN PATENT DOCUMENTS

| | | |
|---|---|---|
| WO | 2005/070481 A1 | 8/2005 |
| WO | 2013044172 A1 | 3/2013 |
| WO | 2017/033193 A2 | 3/2017 |

OTHER PUBLICATIONS

Office Action for corresponding IN application No. 201937041340 dated Feb. 2, 2022, 5 pages.

\* cited by examiner

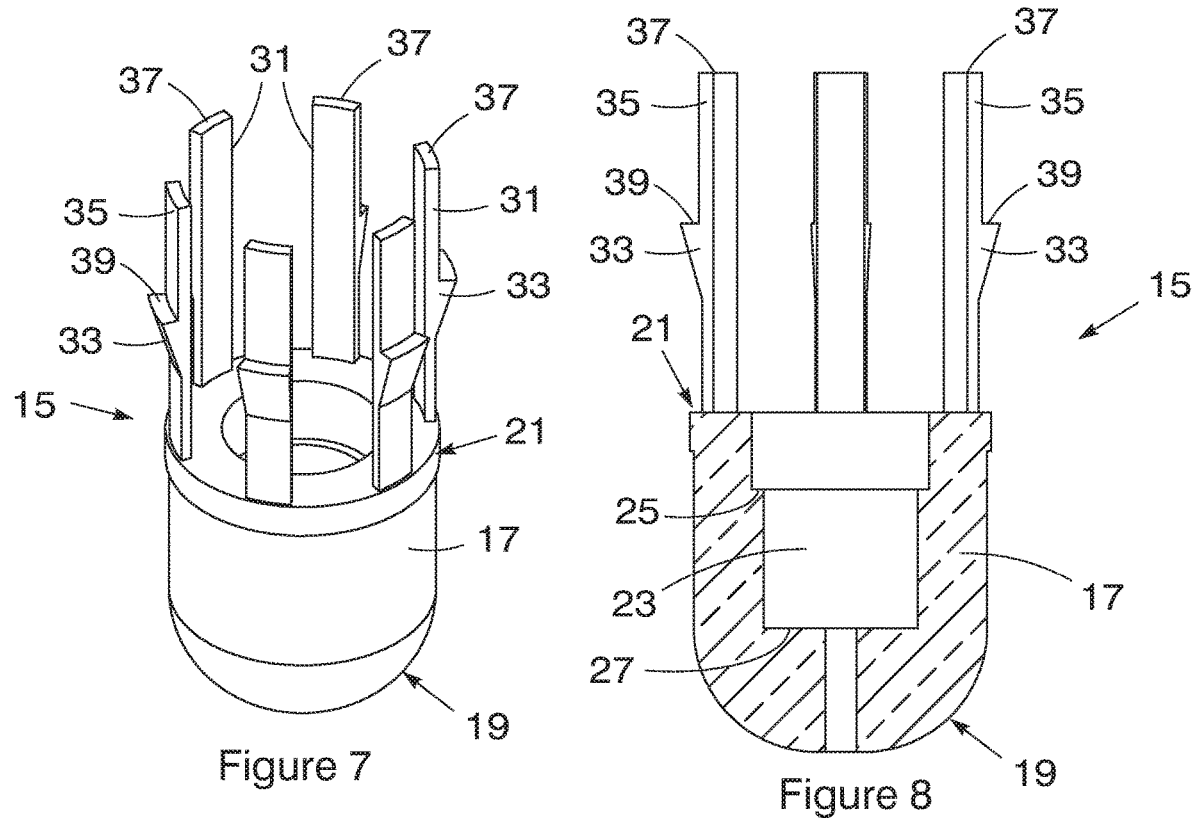
Figure 7
Figure 8
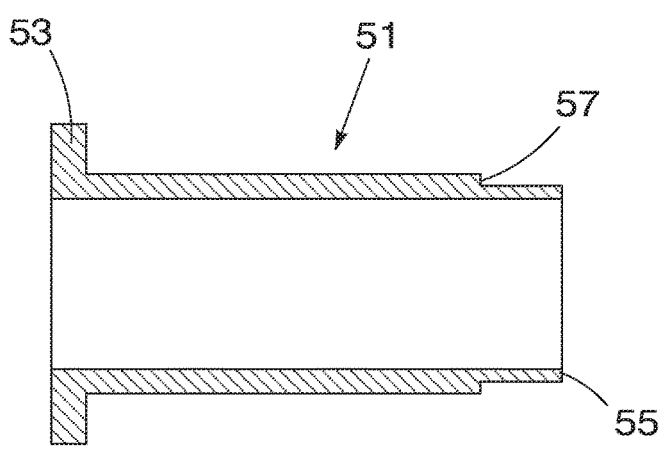
Figure 9

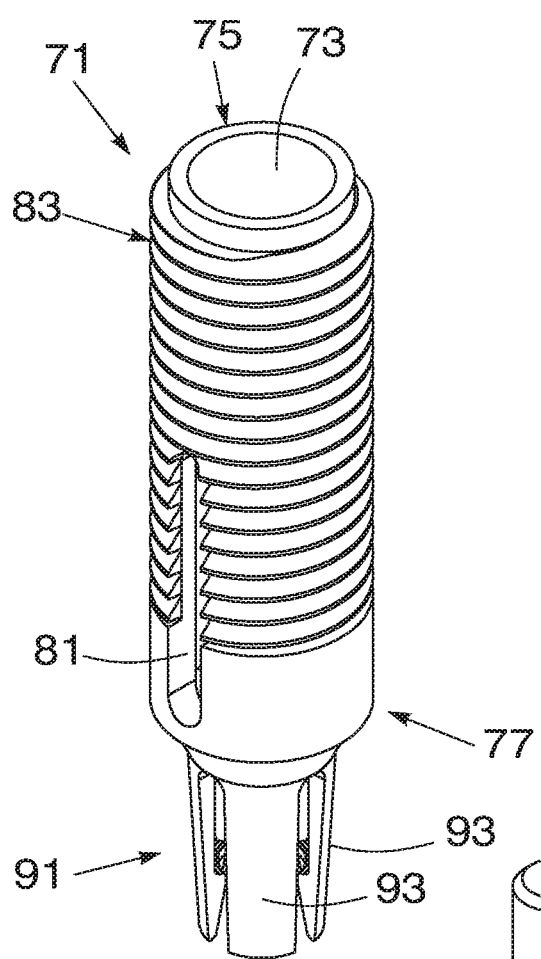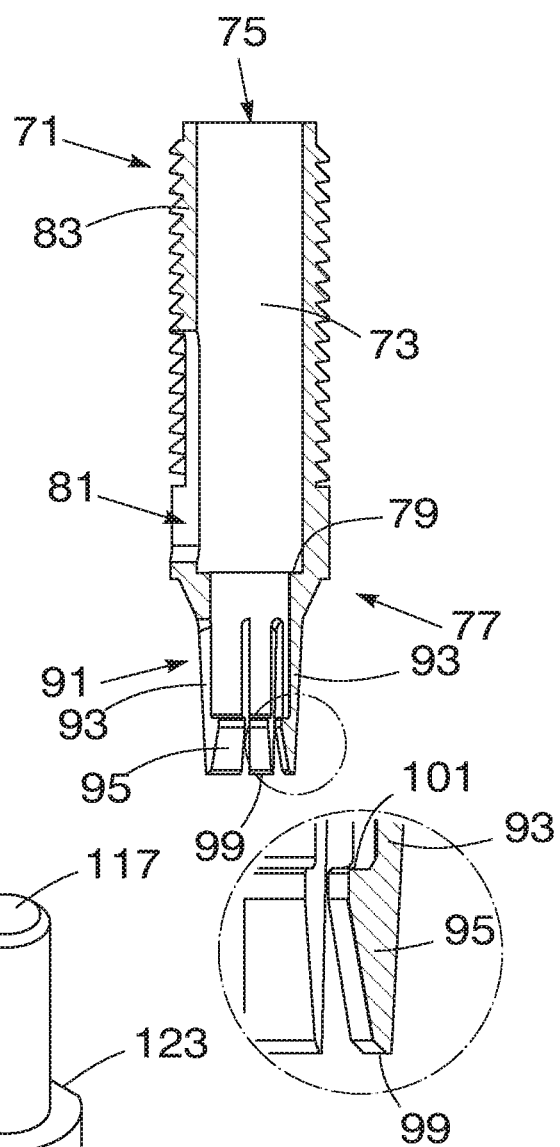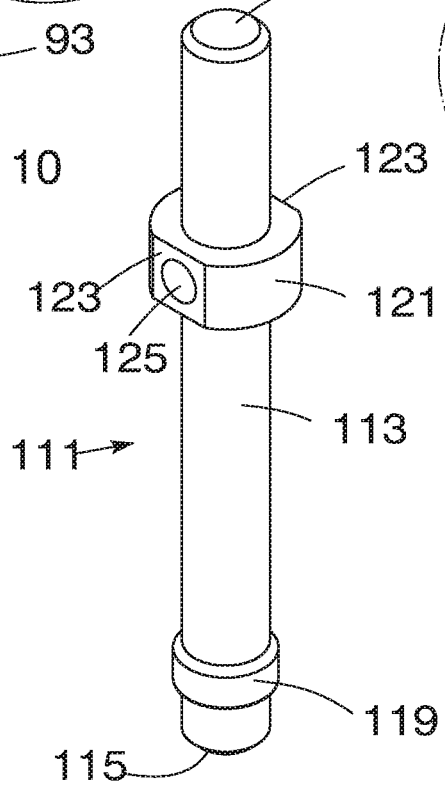
Figure 10
Figure 11
Figure 12

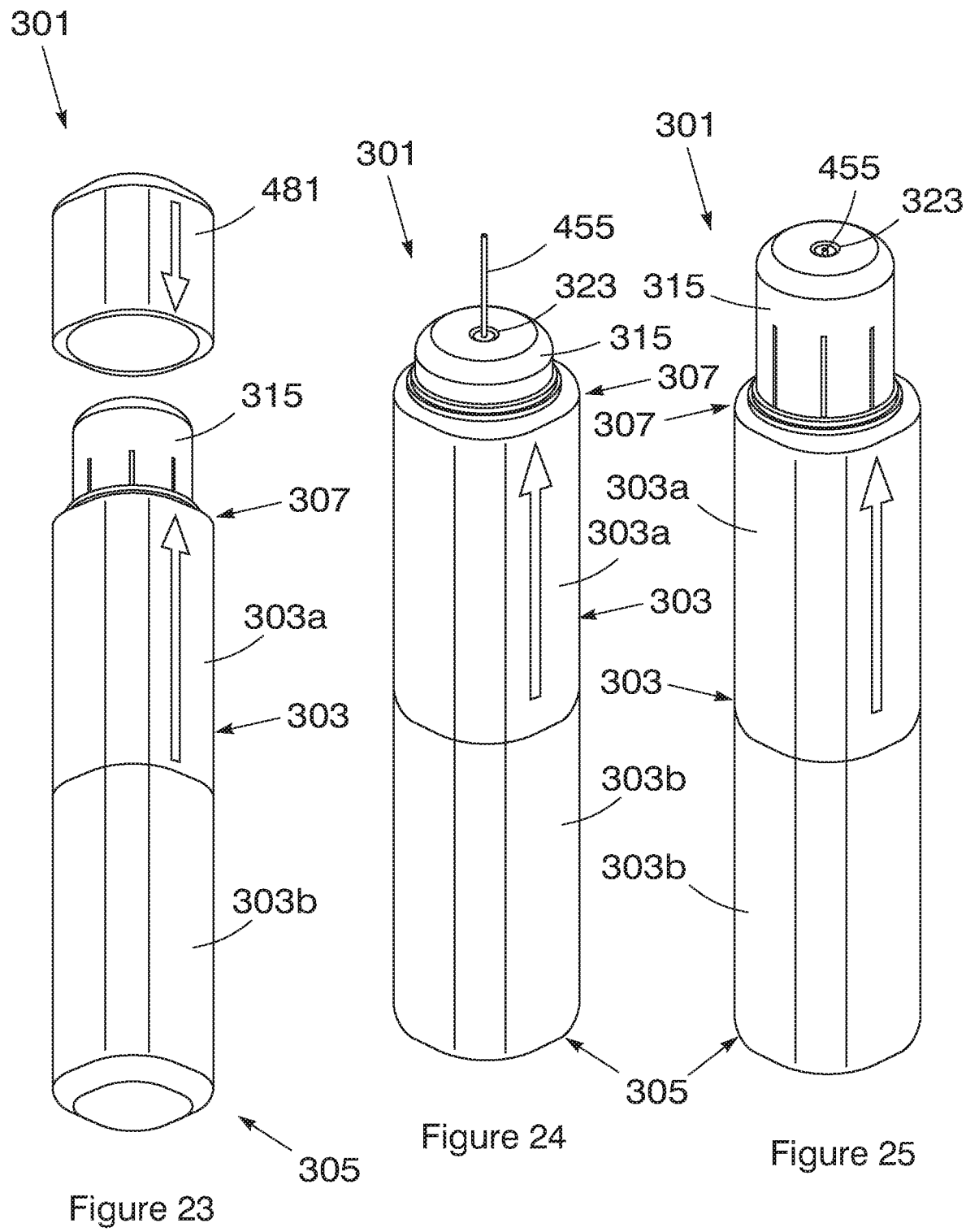

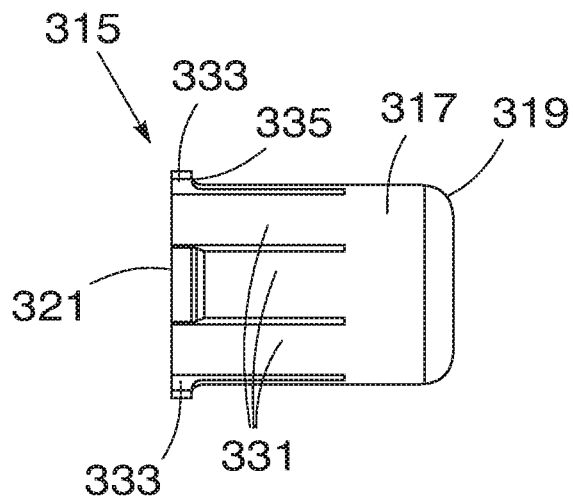
Figure 26
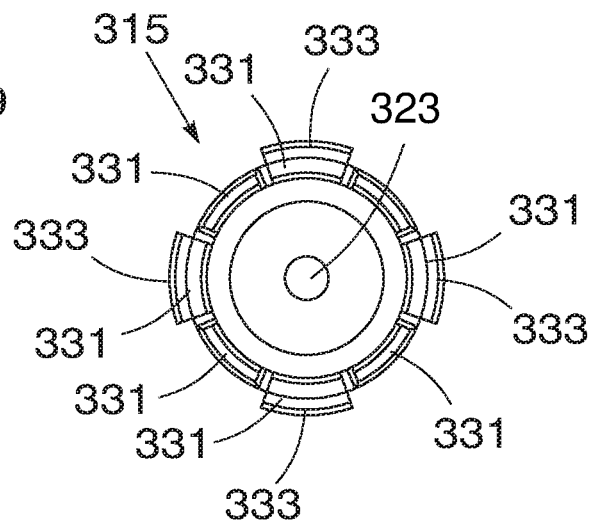
Figure 27
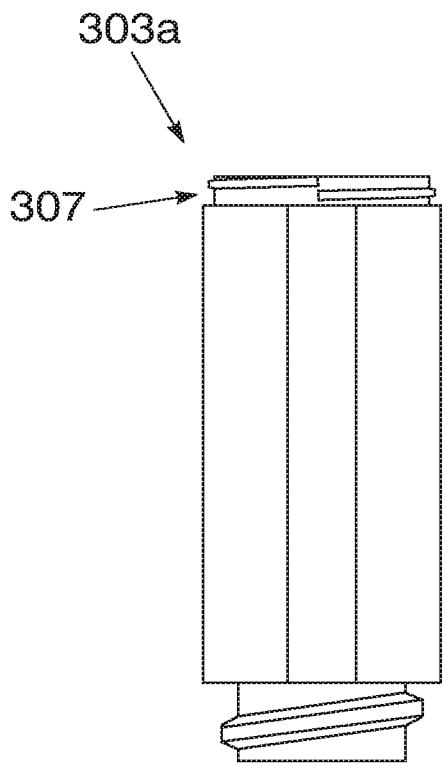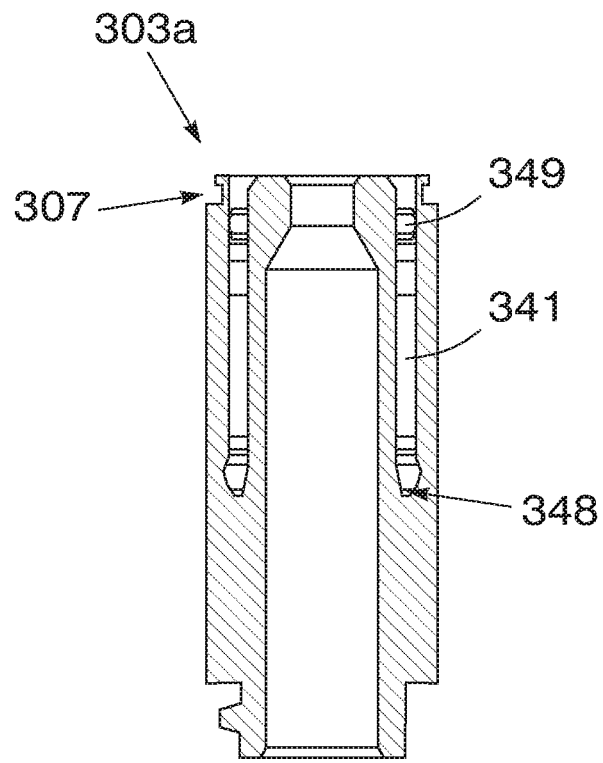
Figure 28

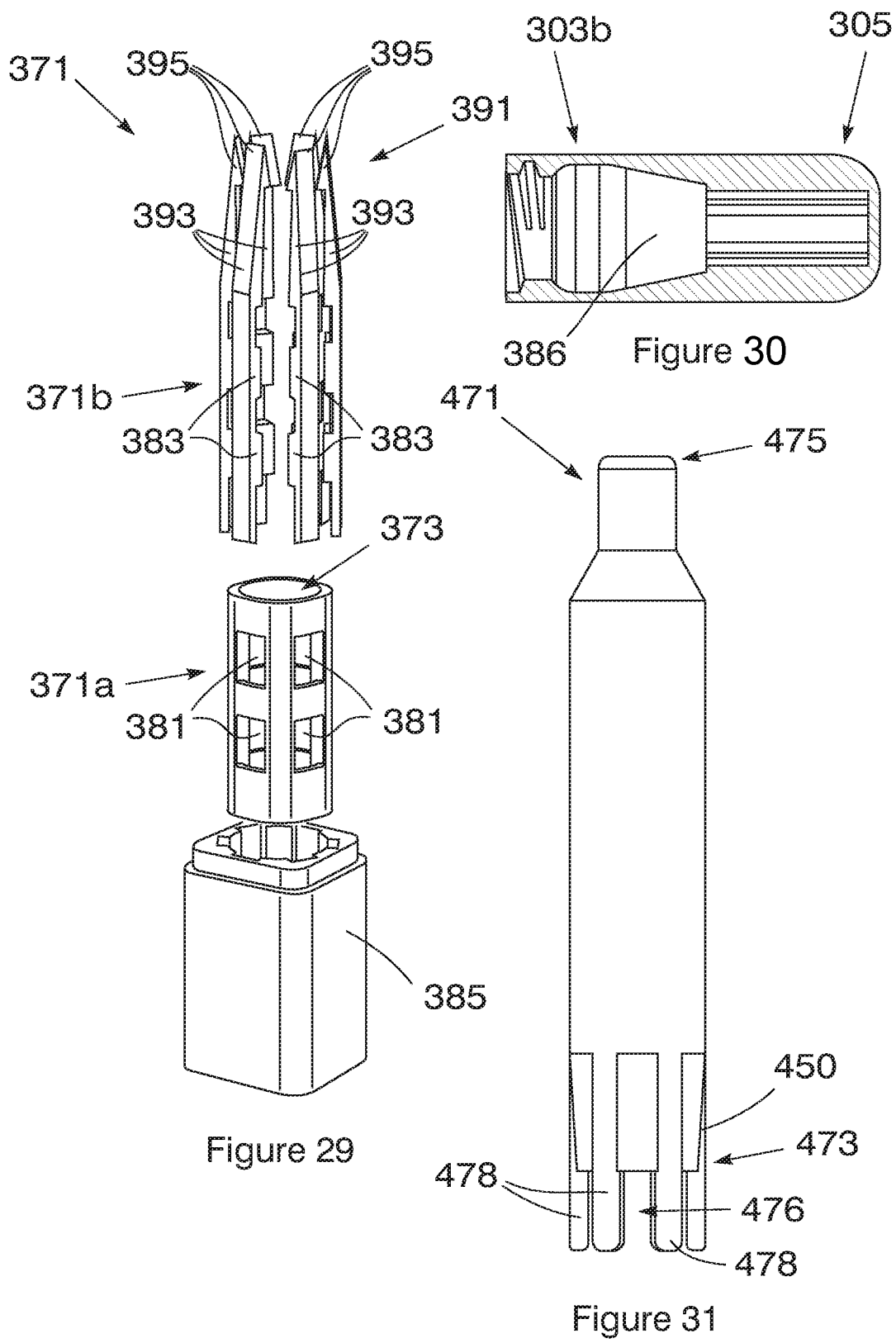

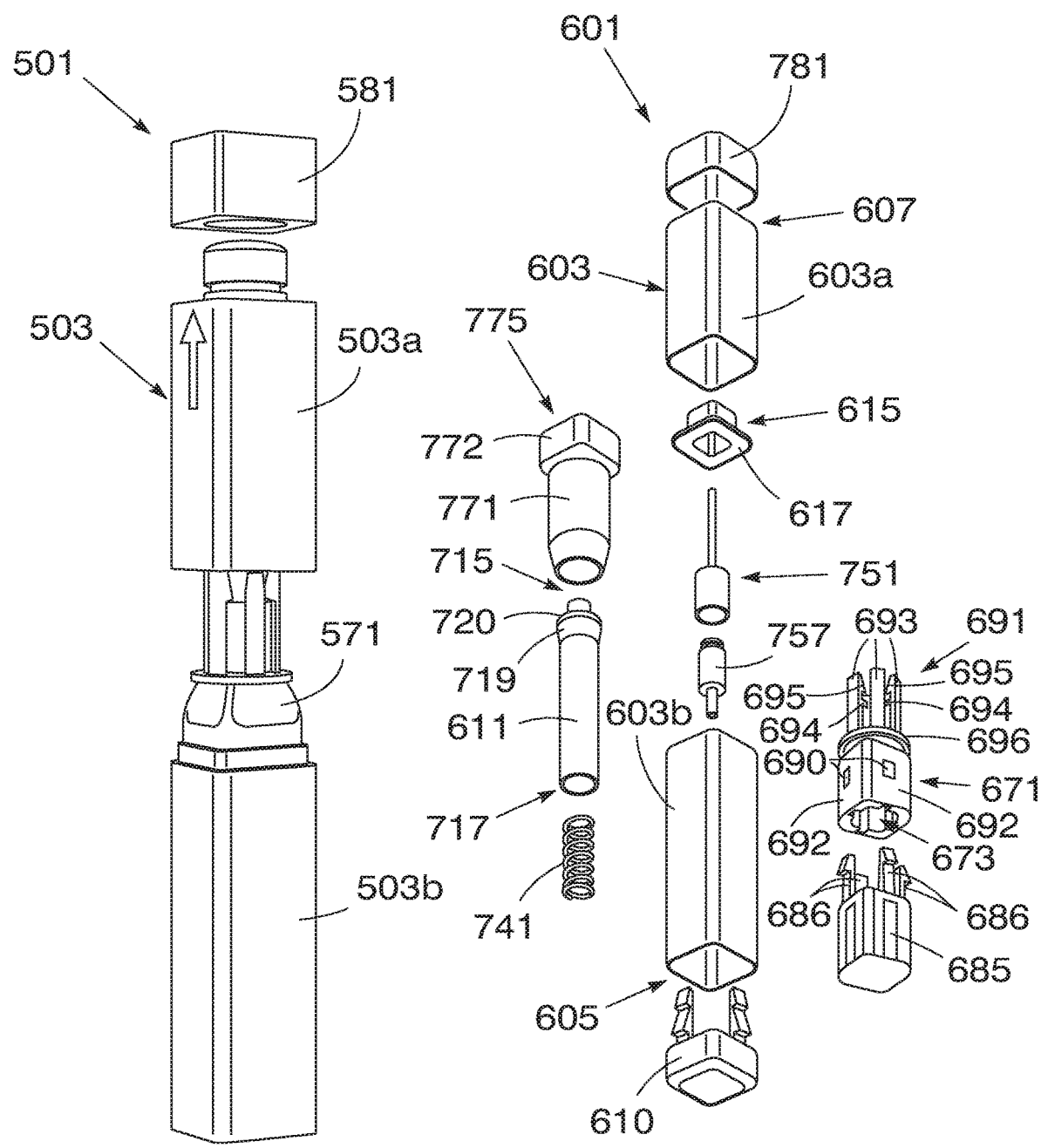

AUTO-INJECTOR

CROSS-REFERENCE TO RELATED APPLICATIONS

This application is a 35 U.S.C. § 371 national phase application of PCT International Application No. PCT/IB2018/051623, filed Mar. 12, 2018, which claims priority to United Kingdom patent application no. 1703982.7 filed Mar. 13, 2017, the disclosures of which are hereby incorporated herein by reference in their entireties.

FIELD OF THE INVENTION

This invention relates to an auto-injector which may be used to inject a drug into a person in need thereof.

BACKGROUND TO THE INVENTION

Auto-injectors are medical devices which deliver a pre-loaded dose of a drug and are usually intended for self-administration or administration by untrained persons. The devices typically employ a spring-loaded syringe which is activated when the device is pushed firmly against the body. They have found widespread use in the intramuscular administration of adrenaline (epinephrine) to patients who suffer from anaphylaxis. They are also now routinely supplied to certain military forces for the administration of drugs used to counter nerve agents or similar biological weapons.

One drawback with especially adrenaline auto-injectors is that the adrenaline expires 18 to 24 months from the date of manufacturing thereof. This means that the entire adrenaline containing auto-injector device must be thrown away and a new one bought whether or not a patient has used it. Given that these devices are generally costly this presents a difficulty for many users.

A further issue is that most auto-injectors do not penetrate to the desired depth within a patient's body. The optimum depth of penetration into muscle will ensure that the medication is absorbed at a faster rate and therefore has a higher probability of saving the patient's life.

Also, most available devices in the market require the user to pull off a safety release at the back of the device and inject themselves with the other side of the device. This causes some confusion as the safety release is in a different location to the activation mechanism. This has resulted in various injuries including injuries caused by injecting with the incorrect side, resulting in a patient injecting his or her thumb or hand instead of the thigh for example.

Many of the available devices require a swing motion of the arm to plunge the auto-injector against muscle thereby activating the device to inject drug into the muscle. It has been found that the swing motion of the arm and the high pressure applied by a user to activate the injection adversely affects the efficiency of drug administration due to ineffective user control and the probability of leakage from a backlash of the auto-injector after impact.

In this specification the term "syringe" shall have its widest meaning and shall include syringes, cartridges, cartridge syringes and any other type of container configured to hold a dose of a drug and having a piston movable therein for discharging the drug from the container. A syringe may be fitted with a needle or may have a needle which extends therefrom.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with this invention there is provided an auto-injector which includes a housing having a handle end and an injection end and a tip extending from the injection end with a syringe received in the housing and slidable between a stowed condition and an active condition, the syringe having a barrel with a piston movable therein and a needle extending therefrom, wherein the needle extends at least partially from the tip with the syringe in the active condition, and wherein the piston is releasably secured to one end of a plunger which is slidably secured within a body in the handle end of the housing and is operable through a bias provided by a motive source in the body from a loaded condition in which it retains the syringe in its stowed condition to a discharged condition in which it acts on the plunger to move the syringe to the active condition and to slide the piston within the barrel to expel the contents of the syringe through the needle, the piston being held in the loaded condition against the bias by a detent extending from the body and which can be selectively released by operation of an actuator which is slidably secured within the housing at least partially over the syringe, the actuator being operated by pressure applied to the tip in the direction of the handle end.

A further feature of the invention provides for the motive source to be a compressible element which is captured between a surface on the plunger and a closure on the body.

Still further features of the invention provide for the detent to include a plurality of outwardly resiliently flexible and circumferentially spaced arms, each having an inclined tooth at or near its end; for the inclined teeth to provide a snap fit over a radially extending shoulder on the plunger; for the actuator to be tubular with a tapered leading end configured to engage the detent internally of the inclined teeth and to displace the arms radially outwardly through axial movement towards the plunger; and for the angle of inclination of the tapered leading end to be selected to require a displacement of the actuator of between about 1 and 5 mm, preferably between about 2 and 5 mm, to displace the arms radially outwardly and release the inclined teeth from the detent.

Yet further features of the invention provide for the tip to have a central passage through which the needle can move; for the tip to be slidably secured within a circumferential groove in an injection end of the housing and to be biased toward an extended condition in which the tip substantially extends beyond the injection end of the housing by a motive source provided in the circumferential groove; for a removable safety cap to be provided on the housing over the tip; and for the housing to be provided by two or more parts which are releasably secured together so that the syringe is replaceable.

An embodiment of the invention will now be described, by way of example only, with reference to the accompanying drawings.

BRIEF DESCRIPTION OF THE DRAWINGS

In the drawings:

FIG. 7 is a three-dimensional view of the tip of the embodiment of FIG. 1;

FIG. 8 is a sectional elevation of the tip of FIG. 7;

FIG. 9 is a sectional elevation of the spacer of the embodiment of FIG. 1;

FIG. 10 is three-dimensional view of the body of the embodiment of FIG. 1;

FIG. 11 is a sectional elevation of the body of FIG. 10;

FIG. 12 is three-dimensional view of the plunger of the embodiment of FIG. 1;

FIG. 23 is a three-dimensional view of the embodiment of FIG. 16 with the safety cap removed;

FIG. 24 is a three-dimensional view of the embodiment of FIG. 16 with the tip receded and the syringe in the active condition;

FIG. 25 is a three-dimensional view of the embodiment of FIG. 16 with the tip extending over the needle with the syringe in the active condition;

FIG. 26 is a side elevation of the tip of the embodiment of FIG. 16;

FIG. 27 is an internal plan view of the tip of the embodiment of FIG. 16;

FIG. 28 is a side elevation and sectional view of the part of the housing at the injection end;

FIG. 29 is an exploded view of the body with the detent that fits in the handle end of the housing of the embodiment of FIG. 16;

FIG. 30 is a sectional side elevation of the handle end of the housing of the embodiment of FIG. 16 that defines a chamber for the body;

FIG. 31 is a side elevation of the actuator of the embodiment of FIG. 16;

FIG. 32 is a three-dimensional view of a fourth embodiment of an auto-injector in a disassembled condition;

FIG. 33 is an exploded view of a fifth embodiment of an auto-injector; and

DETAILED DESCRIPTION WITH REFERENCE TO THE DRAWINGS

Figure 5:
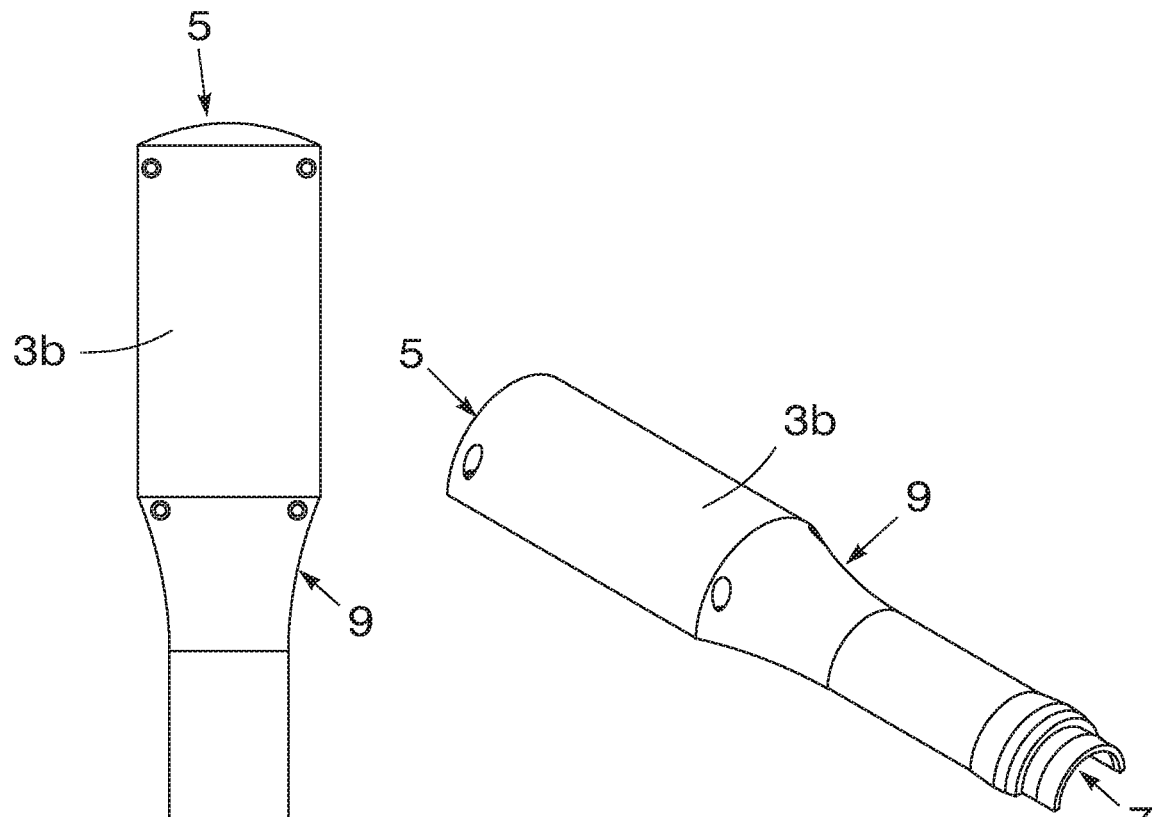
FIG. 5 is an external plan and three-dimensional view of one part of the housing of the embodiment of FIG. 1.
Figure 6:
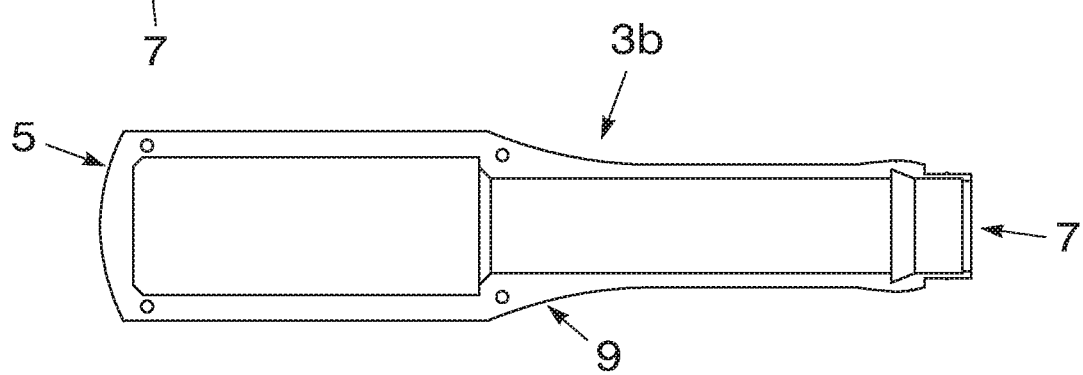
FIG. 6 is an internal plan view a part of the housing of FIG. 5.

An embodiment of an auto-injector (1) is shown in FIGS. 1 to 4 and includes an elongate, generally cylindrical housing (3) having a closed handle end (5) and an open injection end (7). The housing (3) is split longitudinally to form two parts (3a, 3b), as shown more clearly in FIGS. 5 and 6, which are secured together by screws (not shown). A waist (9) is provided centrally of the housing (3) which results in the injection end (7) being radially thinner than the handle end (5).

A tip (15) is secured in the injection end (7) of the housing (3). Referring also to FIGS. 7 and 8, the tip (15) has a cylindrical body (17) with a radiused nose (19) and flat rear (21). A passage (23) extends centrally through the tip (15). A pair of radially inwardly stepped shoulders (25, 27) are provided in the passage (23) spaced apart for the rear (21) and nose (19) respectively so that the passage (23) is of narrow diameter through the nose (19) and then of relatively larger diameter to the rear (21).

Six circumferentially spaced legs (31) extend axially from the rear (21) of the tip (15) from its outer periphery. Each leg (31) is of a thin, generally rectangular shape with an inclined tooth (33) provided centrally on the outer surface (35) thereof. Each tooth (33) inclines radially outwardly towards the free end (37) of the respective arms (33) and terminates in a radially extending shoulder (39).

The legs (31) and part of the tip (15) adjacent the rear (21) fit within the injection end (7) of the housing (3). A complementarily shaped circumferential groove (41) internally of the housing (3) receives the inclined teeth (33) on the legs (31) and prevents their further inward travel when no pressure is being applied to the tip (15).

Referring also to FIG. 9, a tubular spacer (51) locates on the rear (21) of the tip (15) and extends between the legs (31) before terminating in a radial flange (53) which provides a sliding fit within the housing (3). The outer surface of the spacer (51) is inwardly stepped to provide a complementary fit with the tip (15) with the end (55) of the spacer (51) abutting the shoulder (25) in the passage (23) and the rear (21) of the tip abutting the shoulder (57) on the spacer (51). The internal diameter of the spacer (51) is the same as that of the passage (23) between the shoulders (25, 27).

A cylindrical body (71) is located in the handle end (5) of the housing (3). Referring also to FIGS. 10 and 11, the body (71) has a bore (73) extending centrally therethrough from a loading end (75) to a stop end (77). The bore (73) is radially inwardly stepped (79) at the stop end and a longitudinally extending slot (81) is provided in the side of the body (71) from near the stop end (77) to about halfway along the length of the body (71). External screw threading (83) is provided on the body (71) from the loading end (75) to near the stop end (77) and a complementarily threaded closure (85) provided over the loading end (75) to provide a screw fit of the closure on the body.

A detent (91) extends from the stop end (77) of the body (71) and, in this embodiment, includes four circumferentially spaced arms (93). These extend axially and each terminates in an inclined tooth (95) on its inner surface. Each tooth (95) is inclined radially inwardly from the free end (99) of the arm (93) to a radially stepped shoulder (101). Each tooth (95) thus tapers from the inwardly extending shoulder (101) to the free end (99) of the respective arm (93).

A plunger (111) is slidably secured within the body (71). Referring also to FIG. 12, the plunger (111) has a shaft (113) with a first end (115) and a second end (117). A collar (119) extends about the shaft (113) near the first end (115), and a bearing surface (121) is provided about the shaft (113) spaced apart from the second end (117). The bearing surface (121) is collar-like with an outer circumference which provides a sliding fit within the bore (73) and a pair of opposite flats (123) with a diametrically extending aperture (125) provided through the flats (123). A pin (127) is located in the aperture (125) and extends through the slot (81) in the body (71) to provide a guide.

The position of the pin (127) within the slot (81), which is visible externally on the body (71), indicates whether the plunger (111) is in the loaded condition or in a discharged condition. In the loaded condition the pin (127) will be positioned at or near the end of the slot (81) closest to the loading end (75) of the body (71), whereas in the discharged condition the pin (127) will have moved along the slot (81) operating as a guide and will have stopped at a position near the stop end (77) of the body (71). The collar (119) provides a radially extending shoulder and is shaped to slide internally of the arms (93) of the detent (91) up to the inclined teeth (95) which engage the collar (119) to prevent further sliding movement thereof.

A motive source is provided in the body (71) to act on the plunger (111) to move it within the body (71). In this embodiment, the motive source is a compression spring (141) which extends about an end portion of the second end (117) of the shaft (113) within the bore (73) and is captured between the bearing surface (121) and the closure (85). The compression spring (141) provides a bias on the plunger (111) in the direction of the detent (91). The detent (91) holds the plunger (111) against the bias in what shall be termed a loaded condition.

With the closure (85) secured to it, the body (71) provides a snug fit in the handle end (5) of the housing (3) with the detent (91) extending through the waist (9) towards the injection end (7).

Figure 13:
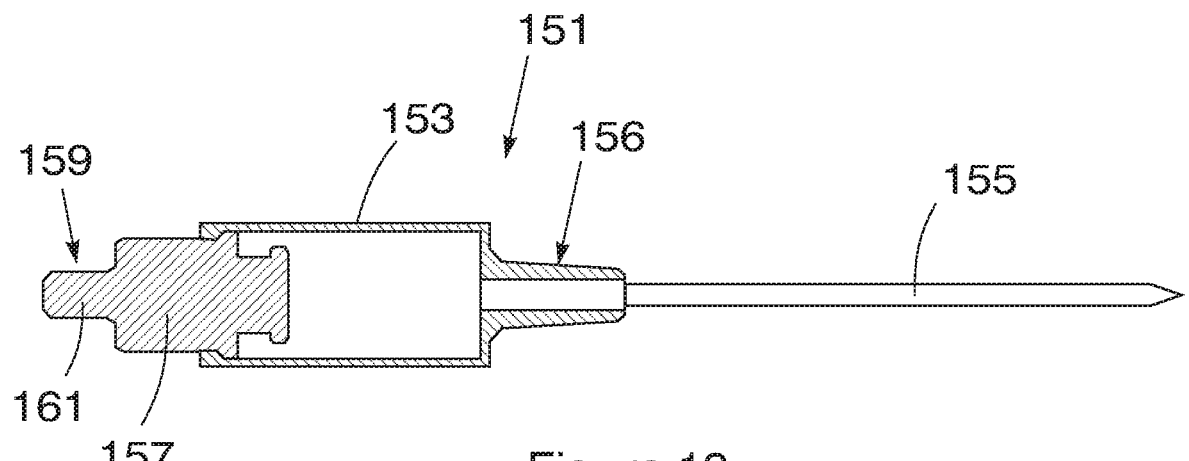
FIG. 13 is sectional elevation of the syringe in the embodiment of FIG. 1.

Referring also to FIG. 13, a syringe (151) extends at least partially between the plunger (111) and the tip (15) and has a barrel (153) with a needle (155) at a narrow end (156) thereof and a piston (157) slidable therein. A reservoir is thus defined in conventional fashion between the piston (157) and barrel (153). The exposed end (159) of the piston (157) is releasably secured to the first end (115) of the plunger (111) while the needle (155) extends through the spacer (51) into the passage (23) in the tip (15). In this embodiment, the piston (157) is secured to the plunger (111) by a lug (161) which extends axially from its free end (159) and provides a press fit to a complementary socket in the first end (115) of the plunger (111).

The wall thickness of the barrel (153) is selected so that the syringe defines a reservoir of a selected volume and can thus hold a selected volume of drug. The piston (157) of the syringe (151) is correspondingly sized to the reservoir to cooperate with the interior of the barrel (153).

A thin protective sheath (not shown) is provided over the needle (155) to prevent contamination of the needle and of the contents of the reservoir. Alternatively or in addition, a sterile sealing sleeve or barrier (not shown) may be provided internally of the barrel of the syringe to seal the reservoir from the environment and prevent any leaks therefrom. When the syringe is moved towards the tip by the plunger the frangible sealing sleeve breaks and the piston is able to expel the drug through the needle.

Figure 14:
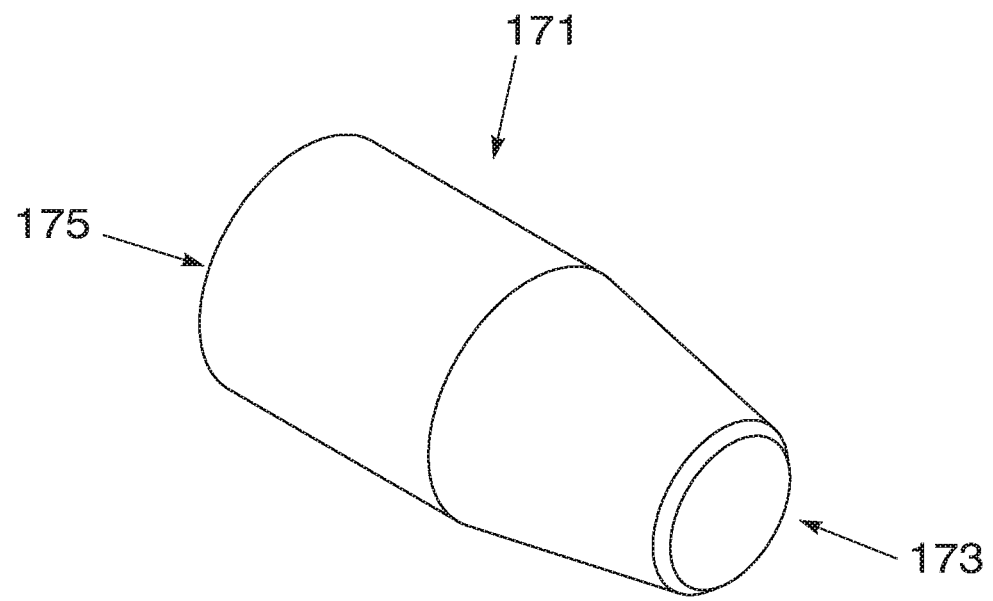
FIG. 14 is a three-dimensional view of the actuator of the embodiment of FIG. 1.

An actuator (171) is slidably secured in the housing (3) over the syringe (151) between the flange (53) on the spacer (51) and the free end (99) of the detent (91). Referring also to FIG. 14, the actuator (171) is tubular and is tapered from about midway along its length towards a leading end (173) which is further bevelled and which fits between the inclined teeth (95) of the detent (91). The trailing end (175) of the actuator (171) is spaced apart from the flange (53) on the spacer (51) and the internal diameter of the actuator (171) is slightly larger than the diameter of the collar (119).

Movement of the actuator (171) towards the detent (91) causes the teeth (95) to be displaced radially outwardly and out of engagement with the collar (119) on the plunger (111). In this embodiment, the teeth (95) are displaced radially outwardly by approximately 0.5 mm. This results in the plunger (111) moving towards the tip (15) under the bias provided by the compression spring (141), to a discharged condition in which the bearing surface (121) abuts the step (79) in the bore (73). With the plunger (111) in the loaded condition, the syringe (151) is held in a stowed condition in which the needle attached to the syringe is fully received or stowed within the tip (15). Movement of the plunger (111) through the bias causes the syringe (151) to slide in the housing (3), within the actuator (171) to an active condition, shown in FIGS. 2 and 3, in which a portion of the needle (155) extends through the passage (23) in the tip (15). The barrel (153) stops at a position in which its narrow end (156) abuts against the shoulder (27) in the tip (15) in the active condition. Whilst in the syringe is in the active condition, the plunger (111) also moves the piston (157) within the barrel (153) to expel the contents of the syringe in the reservoir. The piston (157) moves toward the tip (15) under the bias provided by the compression spring (141) acting on the plunger.

A removable safety cap (181) is a press fit over the injection end (7) of the housing (3) and encloses the tip (15). The safety cap (181) is provided on the injection end (7) to alleviate problems associated with users not knowing which end of the auto-injector is the injection end. The configuration of the auto-injector has been optimised to prevent accidental injury by injecting into a user's own hand or thumb in an emergency situation. Furthermore, the housing (3) is shaped to have a waist (9) and an injection end (7) that is radially thinner than the handle end (5) to intuitively indicate which side of the device injects the drug.

In use, the auto-injector (1) is maintained with the plunger (111) in the loaded condition and the syringe (151) in the stowed condition and filled with an injectable drug such as adrenaline. Any suitable drug may of course be used. With the safety cap (181) in place the auto-injector can be safely carried about or handled without being activated. Where it is desired to use the auto-injector (1) to inject a person with the drug, such as in a case of suspected anaphylaxis, the safety cap (181) is removed to expose the tip (15). Holding the housing (3) about its handle end (5) the user simply presses the tip (15) onto a suitable body part (not shown), such as a thigh or the buttocks. Resistance to inward movement of the tip (15) is provided by inclined teeth (33) on the legs (31) engaging in the groove (41) in the housing (3). Sustained pressure on the tip (15) in the direction of the handle end (5) by the user causes the legs (31) to buckle radially inwardly and the tip (15) to slide into the housing (15) pushing the spacer (51) further into the housing (3) as well. The flange (53) on the spacer (51) in turn engages the trailing end (175) of the actuator (171) which is subsequently pushed towards the detent (91) engaging it internally of the inclined teeth (95). Continued axial movement of the actuator (171) in the direction of the plunger (111) causes it to displace the arms (93) of the detent (91) radially outwardly and causes the teeth (95) to disengage from the collar (119). Under the bias of the compression spring (141) the plunger (111) subsequently moves rapidly to the discharged condition. In doing so the plunger (111) acts on the piston (157) to move the syringe (151) from its stowed condition to its active condition.

Figure 1:
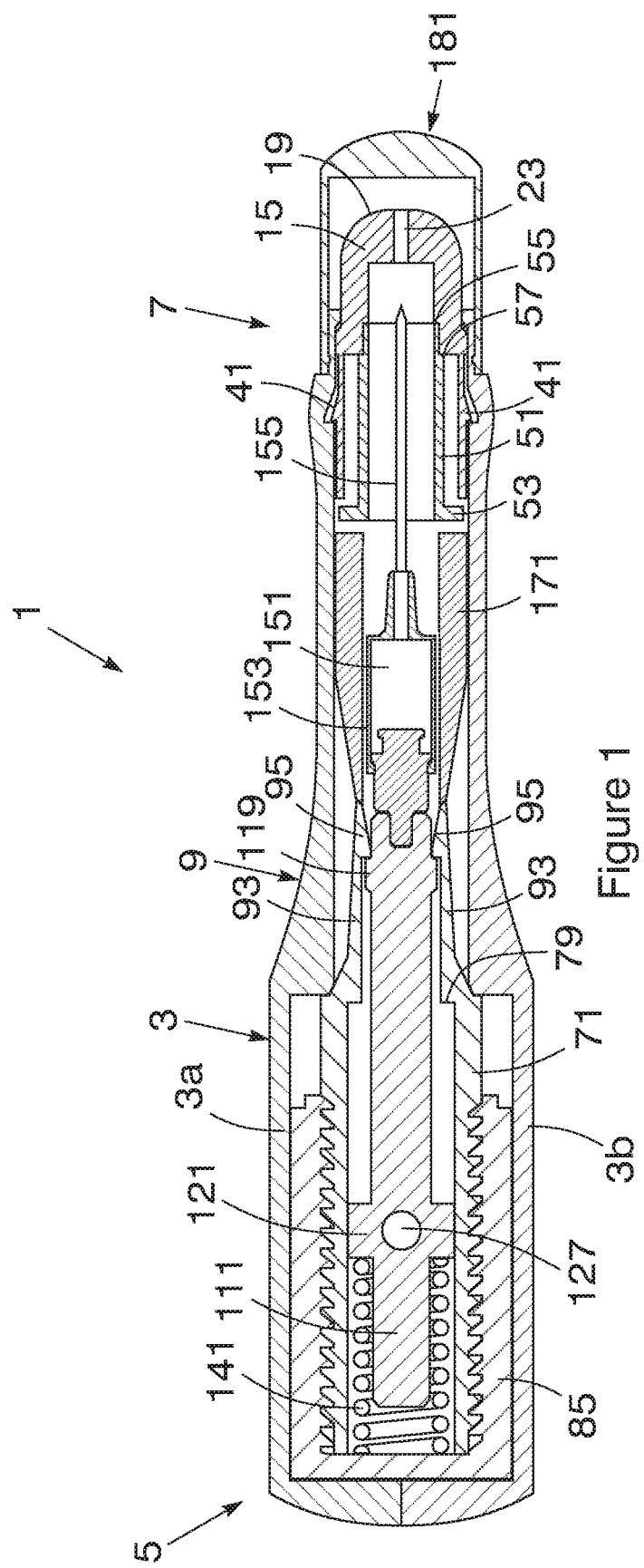
FIG. 1 is a sectional side elevation of an embodiment of an auto-injector with the syringe in a stowed condition and the plunger in a loaded condition.
Figure 2:
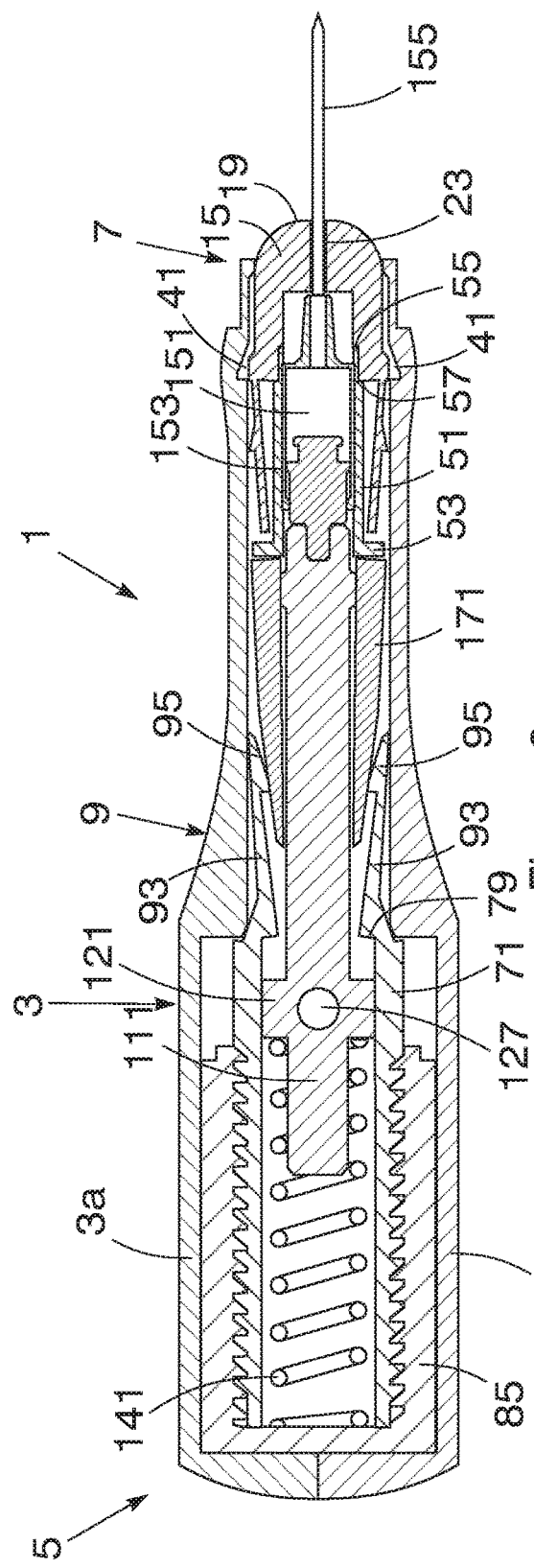
FIG. 2 is a sectional side elevation of the embodiment of FIG. 1 with the syringe in an active condition and the plunger moving towards a discharged condition.
Figure 3:
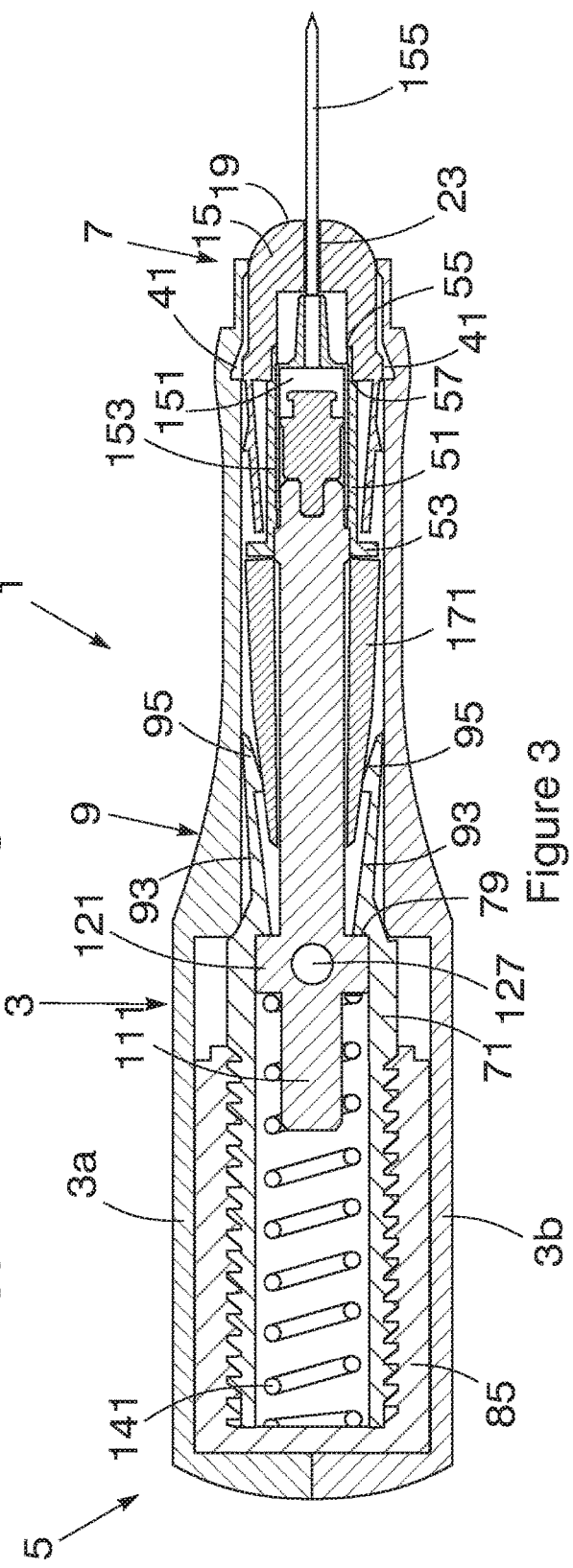
FIG. 3 is a sectional side elevation of the embodiment of FIG. 1 with the syringe in the active condition and the plunger in a fully discharged condition.
Figure 4:
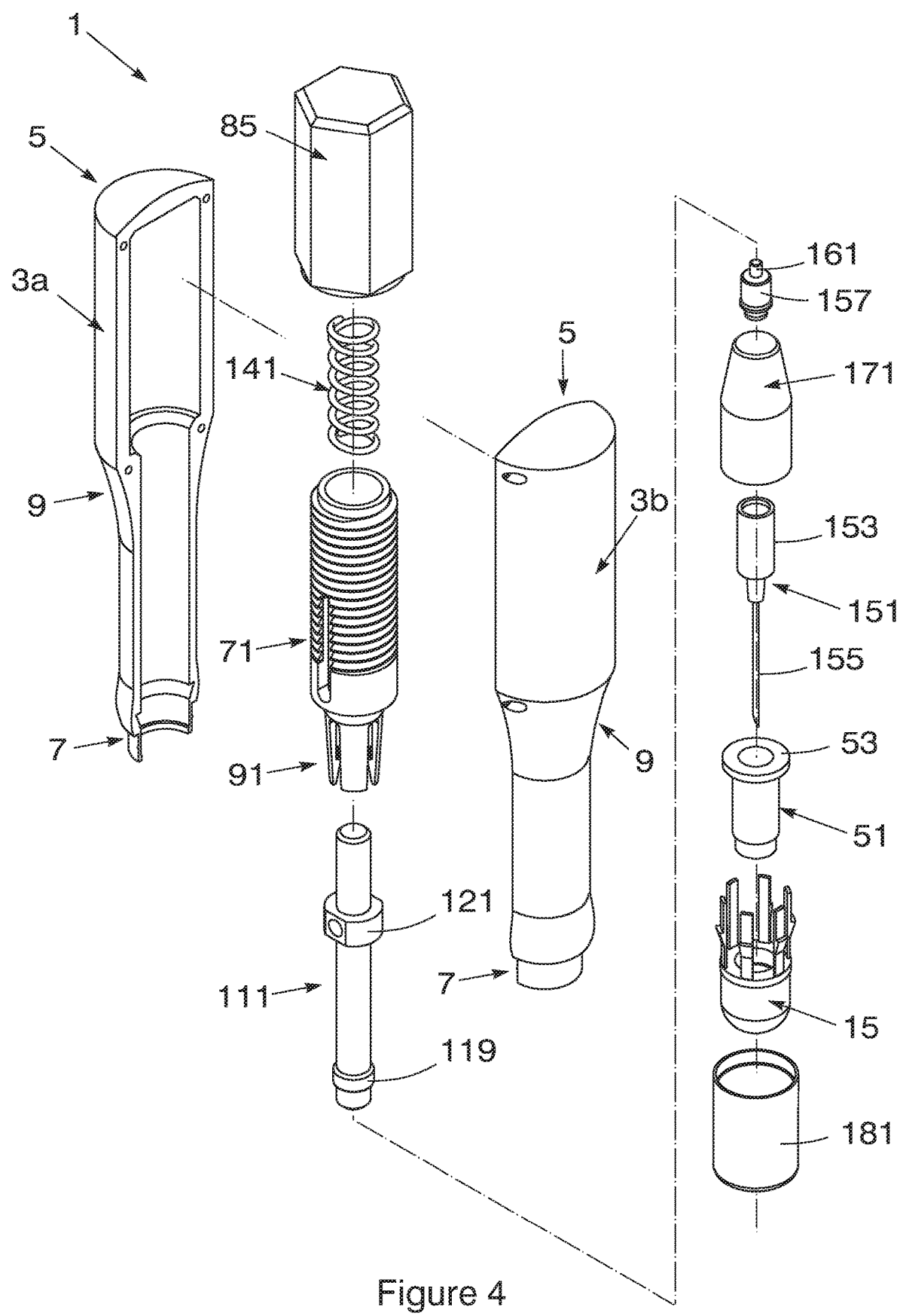
FIG. 4 is an exploded view of the embodiment of FIG. 1.

As the tip (15) is in contact with a body part (not shown) the needle (155) is driven through the passage (23) in the tip (15) into the body part. The needle (155) has a selected length to ensure intramuscular, and not subcutaneous, injection or penetration of the needle into the body part. As the barrel (153) comes to rest in the active condition, as shown in FIGS. 2 and 3, the plunger (111) continues to act on the piston (157) to inject the drug in the syringe (151) into the body part. This occurs very rapidly, i.e. within about 2.5 seconds, as is required of an auto-injector.

A compression spring (141) is used to bias the plunger (111) to move towards the tip (15). The auto-injector (1) makes use of the compression spring (141) for both insertion of the needle into a body part and the injection of the drug into the body part. In this embodiment, a single spring is used for insertion and for dispensing the drug. Consequently, the auto-injector (1) is configured such that the resistance to the movement of the syringe (151) to its active condition is less than the resistance to the movement of the piston (157) within the barrel (153) of the syringe (151). This ensures that the syringe (151) is in the active condition with the needle injected into a body part in use, before the drug is expelled from the needle (155) by the movement of the piston (157) towards the tip (15). The higher resistance to the movement of the piston (157) relative to the plunger results from the shape of the syringe (151) having a narrow end (156) and a needle (155) of an appropriate diameter. Moreover, the thin protective sheath (not shown) that is provided over the needle (155) may also increase the relative resistance to movement of the piston.

Importantly the auto-injector (1) can be used again with a new syringe. This is achieved by opening the housing (3) and removing the tip (15), spacer (51) and actuator (171). The used syringe (151) is then released from the plunger (111) by pulling to disengage the lug (161) from the socket in the plunger (111). Hereafter the closure (85) is partially unscrewed from the body (71) to release pressure on the compression spring (141), if any. This permits the plunger (111) to be pushed back towards the body (71). As the collar (119) engages the inclined surface of the teeth (95) it displaces these radially outwardly until they provide a snap fit over the collar (119) to once more hold it in the loaded condition. The closure (85) is then screwed fully onto the body (71) to compress the spring (141) and provide a bias on the plunger (111).

A new pre-filled syringe or cartridge is then secured to the end of the plunger (111) and the auto-injector reassembled by sliding the actuator (171) over the barrel (153) of the syringe (151) and the spacer (51). Hereafter the housing is secured together; the tip (15) is repositioned to again extend outward from the housing (3) and cover the needle (155) and the safety cap is replaced.

A further important feature is that the syringe can be replaced once the drug has expired. The same steps as above are followed except that the plunger does not have to be moved back to its loaded condition (being in it already). This feature makes the auto-injector highly cost effective as prolonged use only requires replacement of the relatively inexpensive drug-filled syringe.

The auto-injector is reloadable in that a new syringe can be inserted into the body of the auto-injector and the plunger and syringe can be reset to their loaded and inactive conditions, respectively. For this reason the auto-injector and housing are provided by a number of parts which are releasably secured together so as to be capable of being reassembled. The parts of the housing may be configured to open up in any suitable manner to provide access to the resettable components of the auto-injector and to replace the syringe. For example, the housing may be split crosswise into two parts at or near the waist of the housing, instead of longitudinally, and may be releasably secured together by any suitable means to allow reloading of the auto-injector.

The threading of the threaded closure on the loading end of the body results in the compression spring being recompressed with minimal effort. Due to its reloadability, the entire auto-injector need not be disposed of after use which may reduce recurring costs for keeping an auto-injector loaded with an unexpired drug.

The various parts of the auto-injector (except for the syringe) may be made of metal, hard or rigid plastics or any other durable material that allows continued use of the device and fast injections.

A further advantage of the auto-injector is that is can be customised to a user's specific anatomical parameters. For example, a large overweight person requires a greater depth of penetration of the needle for intramuscular injection than does a small, underweight person or child. The depth of penetration can be adjusted by selecting a syringe with an appropriate needle length. The depth of penetration can also be varied as required by changing the distance between the shoulder and the radiused nose of the tip. The length of the slot in the body may also be selected to accommodate movement of the plunger to the required depth of penetration of the needle.

The age of the patient, weight, percentage body fat (fat deposits between the skin and muscle tissue) and blood pressure of a patient amongst other factors have an effect on the depth of injection that is required to ensure that the drug is effectively injected into muscle tissue. The extent of bias provided by the motive source may be varied to ensure that the needle is able to penetrate the skin and muscle tissue before delivering a dosage of a drug into the body. The motive source may be preselected to provide a user specific force of bias. For example, the pressure in the compression spring may be selected for a particular user to obtain a preselected activation force for activation of an injection. The motive source is also customizable based on the selected needle length. The needle length in turn will be selected based on the required depth of penetration for intramuscular injection in a particular user.

The biasing force applied by the motive source to the plunger should be sufficient to overcome frictional forces, penetrate the skin and muscle tissue and overcome forces from the blood pressure of the patient. The greater the force applied to the plunger the faster the rate of injection. A person with high blood pressure, would either require a larger biasing force from the motive source or a slower injection time. The output force of a compression spring used as the motive source can be selected to suit the average blood pressure of the population or may be customised. In one embodiment, the compression spring serving as the motive source is configured to exert a biasing force of about 300 N when fully compressed. As the spring deflects, energy is lost and it was found that a biasing force of about 100 to 150 N remains to move the piston to expel the drug. Computational analysis was used to predict that the time of injection using the auto-injector is about 2.5 seconds.

A syringe may be selected that is suitable for different types of patients to be injected with the auto-injector device. For example, the following four different configurations may be used:
 (1) For babies—0.1 mL dosage, 10 mm depth of injection and 26 gauge syringe needle;
 (2) For children—0.3 mL dosage, 15 mm depth of injection and 26 gauge syringe needle;
 (3) For adults—0.5 mL dosage, 30 mm depth of injection and 24 gauge syringe needle; and
 (4) For obese adults—0.5 mL dosage, 35 mm depth of injection and 25 gauge syringe needle.

The dosage can be increased by increasing the thickness of the walls of the barrel of the syringe and decreasing the diameter of the plunger by a corresponding value, thereby ensuring that the dimensions of the syringe remain the same so that the fit of the syringe within the housing is maintained. This also ensures that the length of the syringe and plunger need not be changed to accommodate different volumes of drug. Accordingly, the device can be customised to inject a selected volume of drug without having to change the length of syringe and the length of the plunger of the device. Similarly, the thickness of the piston wall spanning across the diameter of the barrel may be adjusted depending on the volume of drug to be injected. Alternatively, the dosage can be varied by simply having different concentrations of the active ingredient in the drug.

Further customisation of the auto-injector is possible. For example, the angle at which the actuator is tapered towards the leading end of the actuator can be adjusted in order to adjust the actuation force required to release the teeth from the detent and actuate the plunger and injection mechanism of the auto-injector. The actuation force being the force applied to the actuator when a user presses the tip of the auto-injector against a body part to be injected. A larger angle of inclination relative to the longitudinal axis of the actuator would mean a greater actuating force will be required by the user, as the force component parallel to the axis of the actuator will be larger. A smaller angle of inclination results in greater displacement of the teeth such that a smaller actuating force is required. In one embodiment, an angle of 12° was selected for the tapered end of the actuator which then requires a 2 mm displacement of the actuator in order to trigger the release of the teeth from the detent to activate the injection.

Advantageously, the auto-injector provides so-called "soft" actuation of injection by requiring only minimal pressure applied to the tip to result in a small displacement of the actuator by a few millimetres, preferably by about 1 mm to 5 mm, more preferably between 2 mm and 5 mm, which results in the release of the teeth from the detent to activate the injection. The auto-injector therefore does not require a user to swing his or her arm to plunge the auto-injector against muscle at high pressure to activate the device. Instead, the device can be pressed gently against the skin to apply a small amount of pressure to the tip to activate injection. Thereafter, the motive source is configured to provide a sufficient force of bias to the plunger to ensure intermuscular penetration of the needle and discharge of the drug into the muscle. The device makes use of the internal motive source such as a spring force to result in an injection instead of an externally applied "swing" force.

It will be appreciated that many other embodiments of an auto-injector exist which fall within the scope of the invention, particularly regarding the shape and configuration thereof. For example, the motive source can be provided by a compressed gas instead of a compression spring. The diameters of the barrel and the needle, as well as the needle length, determine the force needed to be exerted by the motive source, amongst other factors. Also, the tip could be configured to act directly on the actuator instead of through a spacer, and a compression spring could be used to bias the tip outwardly. The tip may be provided with any number of circumferentially spaced legs that extend axially from the rear of the tip to provide any suitable number of inclined teeth which cooperate with the groove in the housing for retaining the tip in position before activation of the auto-injector. The syringe can be secured to the plunger in any suitable manner and can be filled with any suitable drug.

Figure 15:
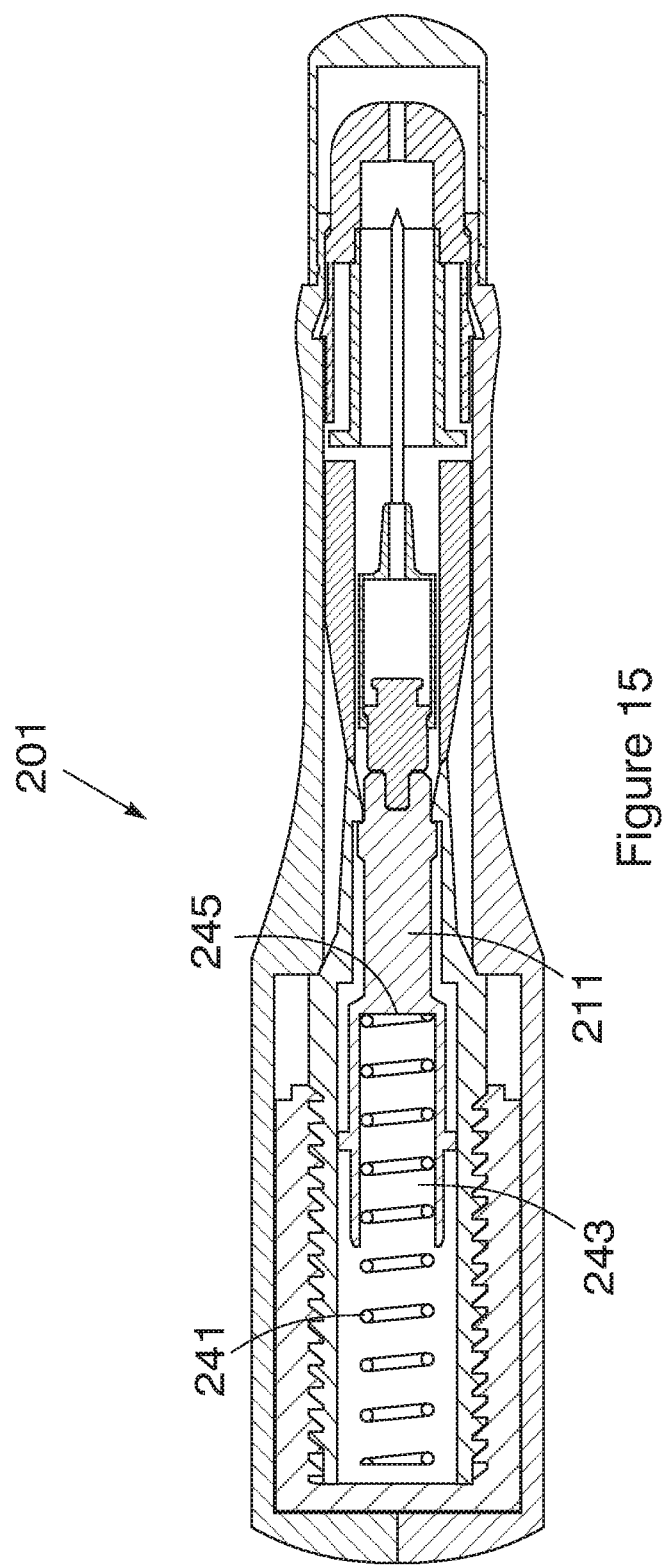
FIG. 15 is a sectional side elevation of a second embodiment of an auto-injector with the syringe in a stowed condition and the plunger in a loaded condition.
Figure 16:
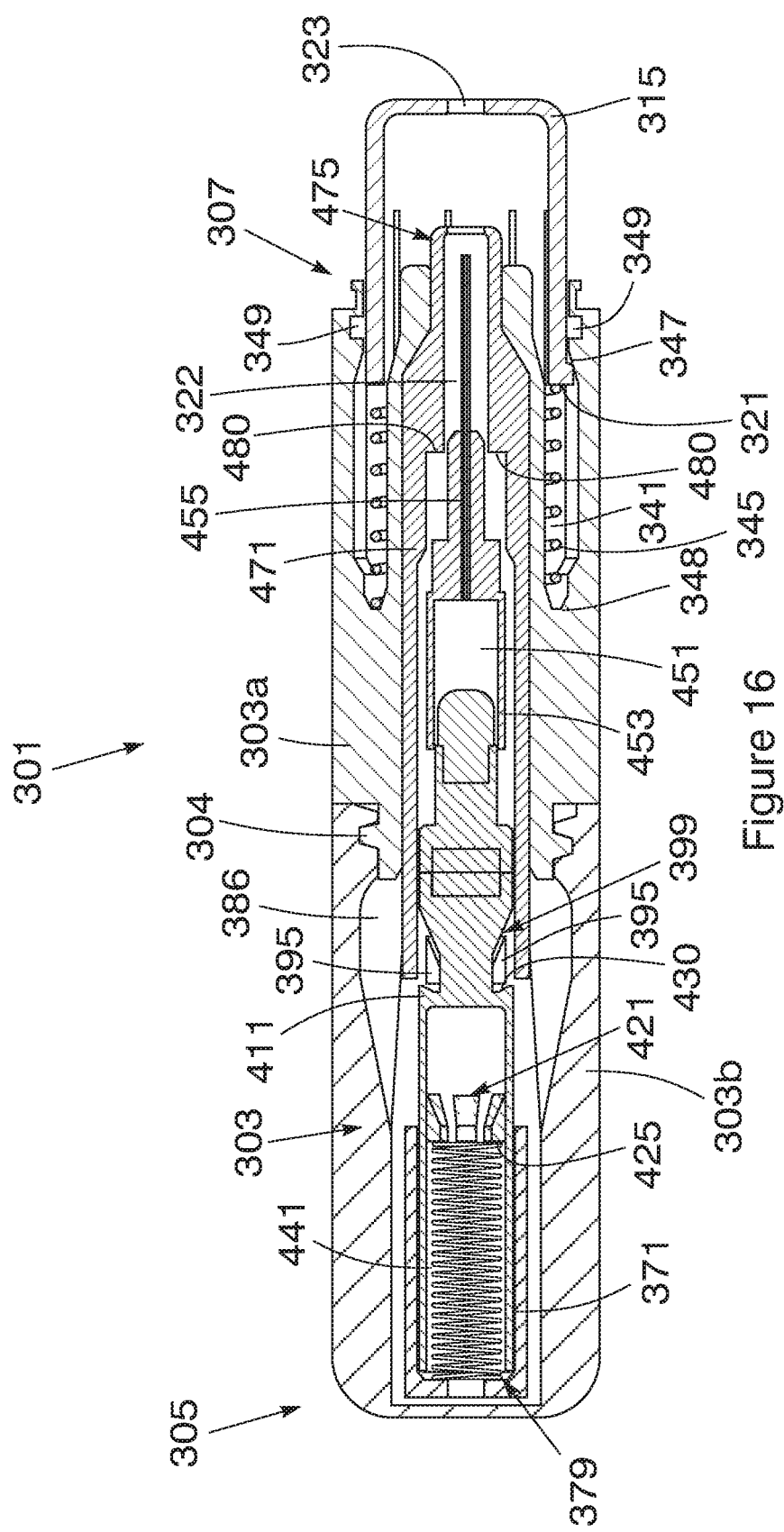
FIG. 16 is a sectional side elevation of a third embodiment of an auto-injector.

The plunger may be configured to cooperate with the motive source which moves it in any appropriate manner. For example, in the event that the motive source is a compression spring, the spring may be held externally or internally of the plunger. A second embodiment of an auto-injector (201) is shown in FIG. 15 and includes a compression spring (241) that extends at least partially within an elongate recess (243) defined within the plunger (211). The compression spring (241) exerts a force on the surface at the pit (245) of the recess (243) to move the plunger from the loaded condition to the active condition. The use of a spring that locates within the recess (243) extending along the length of the plunger (211) assists in minimizing the overall length of the auto-injector.

A third embodiment of an auto-injector (301) is shown in FIGS. 16 to 25. The auto-injector (301) has a different configuration to the previously described embodiments, however the mode of action, in particular the soft-activation mechanism is substantially the same. The auto-injector (301) includes an elongate, generally cylindrical housing (303) having a closed handle end (305) and an open injection end (307). The housing (303) is split transversely or crosswise to form two parts (303a, 303b), which are secured together by a screw fit (304).

A tip (315) is secured in the injection end (307) of the housing (303). Referring also to FIGS. 26 and 27, the tip (315) has a cylindrical body (317) with a radiused nose (319) and flat rear (321). A passage (323) extends centrally through the tip (315). Eight circumferentially spaced legs (331) extend from the tip (315). Each leg (331) is of a thin, generally rectangular shape and four of the legs include radially outwardly extending projections (333) on the outer surface (335) thereof. The four legs (331) with projections (333) provide deflecting members and are arranged to cooperate with recesses defined in the injection end (307) of the housing (303). Referring to FIG. 28, the open injection end (307) of a part (303a) of the housing (303) has a circumferential groove (341) internally thereof in which the legs (331) and part of the tip (315) are slidably received. Referring to FIG. 16 again, the circumferential groove (341) includes a second motive source or biasing means in the form of a spring (345) that is arranged between the flat rear (321) of the tip (315) and the end (348) of the groove (341). The spring (345) biases the tip (315) generally outward so that it extends from the housing (303) beyond the injection end (307) and provides slight resistance against the inward travel of the tip (315) when pressure is applied to it. The circumferential groove (341) is shaped to define an inclined abutment surface (347) that abuts the projections (333) and holds the tip (315) in an extended condition, in which a substantial portion of the tip (315) extends from the housing (303), against the biasing force of the spring (345) when no pressure is applied to the tip (315). The housing (303) further has a secondary recess (349) between the injection end (307) and the inclined surface (347) that receives the projections (333) of the deflecting members and lock the tip (315) in position relative to the housing (303) following activation of the auto-injector (301), thereby covering the needle (455) that extends from the housing (303) when the syringe (451) is in the active condition.

A cylindrical body (371) is located in the handle end (305) of the housing (303). Referring also to FIGS. 29 and 30, the body (371) has two parts, a first part (371a) that has a bore (373) extending centrally therethrough and a plurality of apertures (381) in its side that are arranged to receive complementarily shaped lugs (383) on the second part (371b). The second part (371b) is provided by six arms (393), each having a pair of lugs (383) spaced along its length. The lugs (383) provide, in use, a friction fit in the apertures (381) provided in the first part (371a) which are arranged so that the arms (393) are circumferentially spaced about the first part (371a) when the two parts are attached together. The first part (371a) fits inside the closure (385). The closure (385) fits snugly in the handle end (305) of the housing (303). The part (303b) of the housing shown in FIG. 30 defines a chamber (386) for the body (371) that is shaped to allow for the deflection of the six arms (393) radially outwardly relative to the body (371).

The second part (371a) having the six circumferentially spaced arms (393) provides the detent (391) that extends from the body (371). These extend axially and each terminates in an inclined tooth (395) on its inner surface. The teeth (395) perform the same function in this embodiment as described above with reference to the first embodiment.

Figure 17:
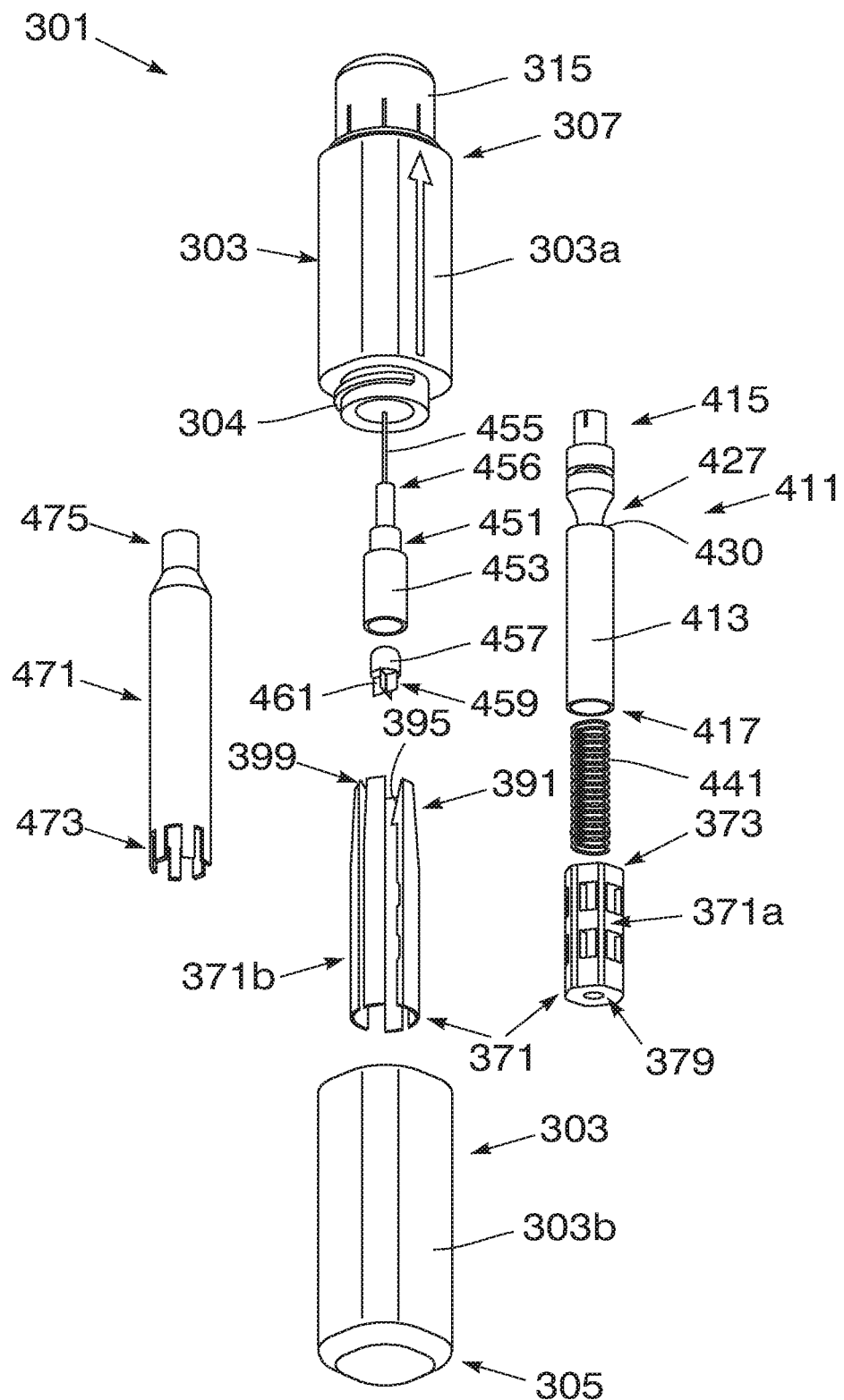
FIG. 17 is an exploded view of the embodiment of FIG. 16.

A plunger (411) is slidably secured within the body (371). Referring also to FIG. 17, the plunger (411) has a shaft (413) with a first end (415) and a second open end (417). The shaft (413) has an outer circumference which provides a sliding fit within the bore (373) of the body (371). In this embodiment the shaft (413) is hollow near its second end (417) so as to house the compression spring (441) therein. An internal surface of the shaft (413) defines a stop formation (421), shown in FIGS. 16 and 18 to 22, consisting of circumferentially arranged teeth-like formations (423) providing radially extending shoulders (425) on which the motive source acts to move the plunger (411).

The plunger has a neck portion (427) near the first end (415) that narrows or tapers towards the second end (417) and terminates in a radially extending shoulder (430) that engages the inclined teeth (395) of the detent (391) to prevent sliding movement of the plunger (411).

The compression spring (441) is captured between the substantially closed end (379) of the body (371) providing a closure and the stop formation (421) on an internal surface of the plunger (411) so as to act on the plunger (411) to move it within the body (371). The compression spring (441) provides a bias on the plunger (411) in the direction of the detent (391). The detent (391) holds the plunger (411) against the bias in the loaded condition.

The body (371) provides a snug fit in the handle end (305) of the housing (303) with the detent (391) extending towards the injection end (307).

A syringe (451) extends at least partially between the plunger (411) and the tip (315) and has a barrel (453) with a needle (455) at a narrow end (456) thereof and a piston (457) slidable therein.

The exposed end (459) of the piston (457) is releasably secured to the first end (415) of the plunger (411) while the needle (455) extends into a passage (322) in the actuator. The piston and plunger are attached by complementary attachment formations. In this embodiment, the piston (457) is secured to the plunger (411) by a cross-shaped lug (461) which extends axially from its free end (459) and provides a press fit to a complementary cross-shaped socket in the first end (415) of the plunger (411).

The actuator (471) of this embodiment is longer than that of the first embodiment so as to extend over the entire syringe and beyond the injection end of the needle (455) in the loaded condition of the syringe (451). The tip (315) therefore acts directly on the actuator, alleviating the need to include a spacer as is present in the first embodiment. The actuator (471) is slidably secured in the housing (303) over the syringe (451) and needle (455) and between tip (315) and the free end (399) of the detent (391). Referring also to FIG. 31, the actuator (471) is tubular and is tapered near and towards a leading end (473) which is further bevelled and which fits between the inclined teeth (395) of the detent (391). The leading end (473) is further provided with guiding grooves (476) defined by circumferentially spaced legs (478) extending beyond the tapered surface (450) and leading end (413) of the actuator (471). The guiding grooves (476) guide the actuator-detent interaction.

The trailing end (475) of the actuator (471) narrows and defines a passage (322) for the needle (455). The trailing end (475) is spaced apart from the tip (315). The internal diameter of the actuator (471) is slightly larger than the diameter of the piston (411) so that the piston can move therein. The inner surface of the actuator (471) is inwardly stepped and the radial shoulder (480) of the step is arranged to abut against the syringe (451) in the active condition of the syringe (451) to stop its movement in the direction of the injection end (307).

The manner of activation of the auto-injector (301) is similar to that of the first embodiment (1). However, the auto-injector (301) is not configured to allow second or further injections using the same device. The syringe (451) containing a drug, such as adrenaline, can still be replaced prior to activation. However, after use, the auto-injector (301) is not meant to be reloaded to be activated again. This particular embodiment of the auto-injector (301) still allows for the replacement of a syringe (451) containing an expired drug, alleviating the need to periodically replace the entire auto-injector when it has not been used, which can be costly.

Figure 18:
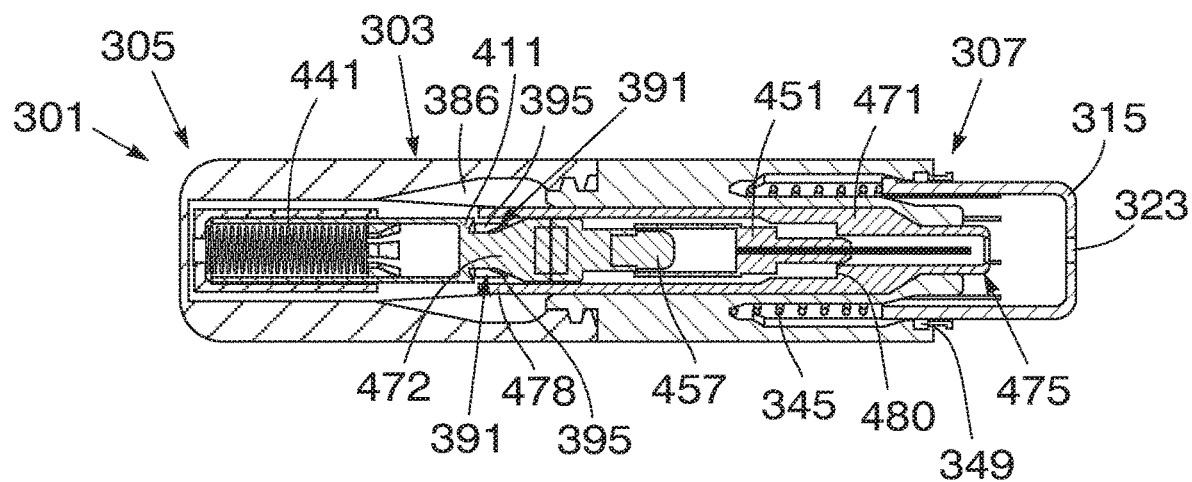
FIG. 18 is a sectional side elevation of the embodiment of FIG. 16 with the syringe in the stowed condition and the plunger in the loaded condition.
Figure 19:
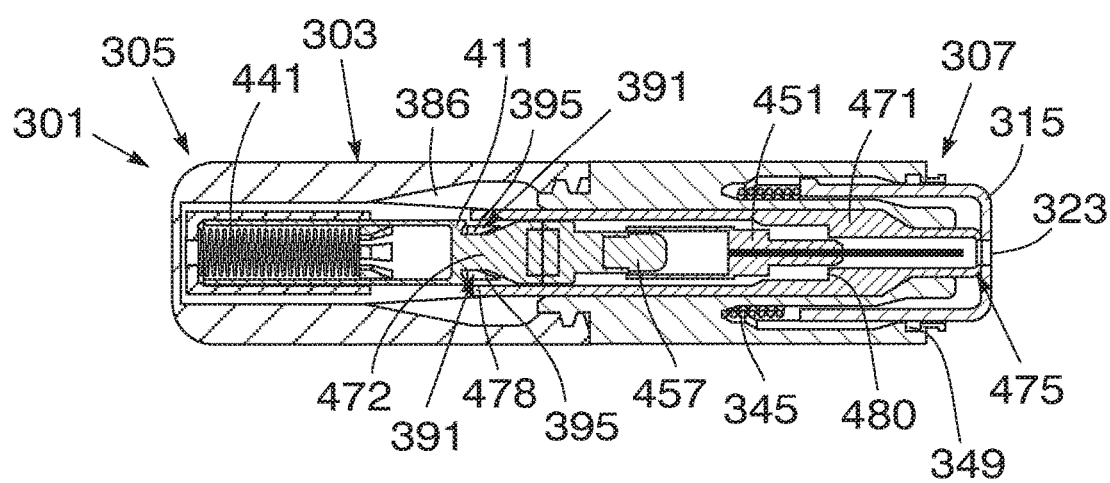
FIG. 19 is a sectional side elevation of the embodiment of FIG. 16 with the tip having travelled inward so as to abut against the actuator.
Figure 20:
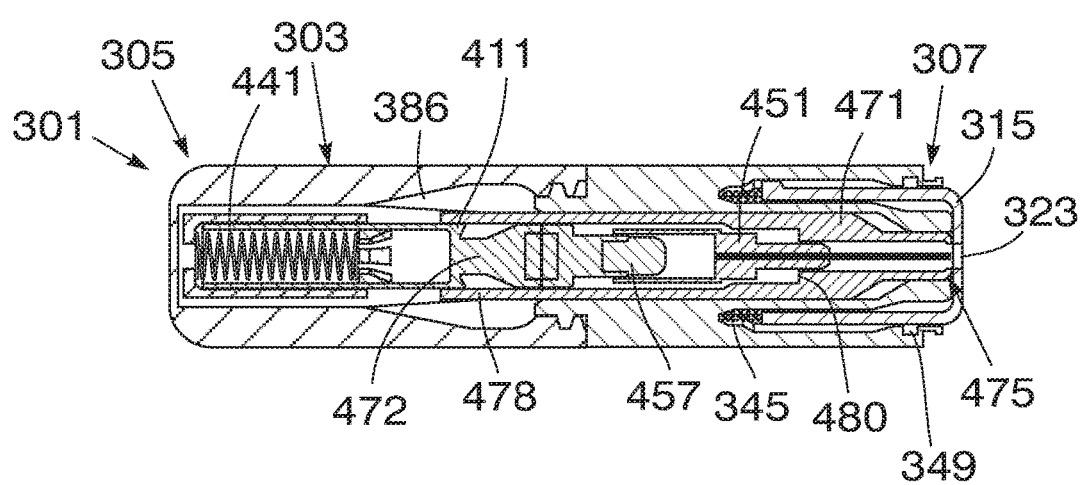
FIG. 20 is a sectional side elevation of the embodiment of FIG. 16 with the tip having travelled further inward, the actuator having displaced the detent and the plunger moving towards a discharged condition.

The activation of the auto-injector (301) is shown stepwise in cross-section in FIGS. 18 to 22 and in three dimensions in FIGS. 23 to 25. The auto-injector (301) is maintained with the plunger (411) in the loaded condition and the syringe (451) in the stowed condition as shown in FIG. 18. With reference to FIG. 23, the safety cap (481) is removed to expose the tip (315). Holding the housing (303)

about its handle end (305) the user presses the tip (315) onto a suitable body part. Resistance to inward movement of the tip (315) is provided by the spring (345) as shown in FIG. 19. Sustained pressure on the tip (315) in the direction of the handle end (305) by the user causes the tip (315) to slide into the housing (303) abutting against the trailing end (475) of the actuator (471) and pushing the actuator (471) further into the housing (303) as well, as shown in FIG. 20. The tapered end (473) of the actuator (471) that is internal of the guiding legs (478) is pushed towards the detent (391) engaging it internally of the inclined teeth (395). Continued axial movement of the actuator (471) in the direction of the plunger (411) causes it to displace the arms (393) of the detent (391) radially outwardly into the space provided by the chamber (386) and causes the teeth (395) to disengage from the radially extending shoulder (430) of the neck portion (427). Under the bias of the compression spring (441), the plunger (411) subsequently moves rapidly to the discharged condition. In doing so the plunger (411) acts on the piston (457) to move the syringe (451) from its stowed condition to its active condition.

Figure 21:
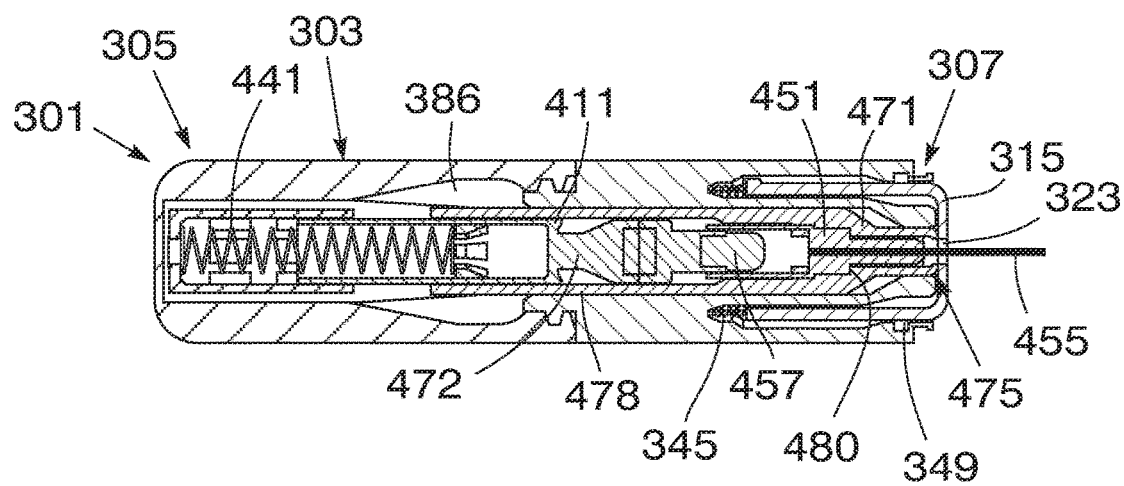
FIG. 21 is a sectional side elevation of the embodiment of FIG. 16 with the syringe in the active condition and the plunger moving towards a discharged condition.
Figure 22:
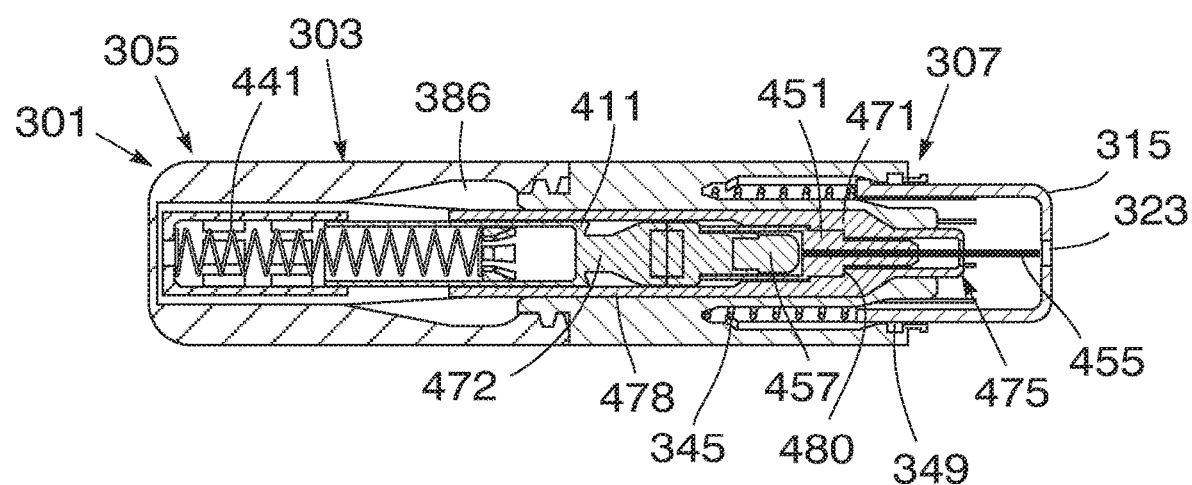
FIG. 22 is a sectional side elevation of the embodiment of FIG. 16 with the syringe in the active condition, the plunger in a fully discharged condition and the needle safely covered by the tip.

As the tip (315) is in contact with a body part (not shown) the needle (455) is driven through the passage (323) in the tip (315) into the body part for intramuscular injection, as shown in FIGS. 21 and 24. As the syringe (451) comes to rest against the shoulder (480) in the active condition, as shown in FIGS. 21 and 22, the plunger (411) continues to act on the piston (457) to rapidly inject the drug in the syringe (451) into the body part. As soon as the pressure is removed from the tip (315) by moving the auto-injector away from the body part following an injection, the spring (345) biases tip (315) outward so as to cover the needle extending beyond the housing (303) as shown in FIGS. 22 and 25. The tip (315) is then locked in this safe position when the projections (333) of the tip (315) are received within the secondary recess (349) defined in the housing (303).

Importantly, the syringe (451) can be replaced, provided the auto-injector (301) has not yet been used or activated. This is achieved by opening the housing (303), removing the syringe (451) by disconnecting it from the plunger (411) and replacing it with a new pre-filled syringe or cartridge that is then secured to the end of the plunger (411) again. The auto-injector can be reassembled by sliding the actuator (471) over the syringe (451). Hereafter the housing (303) is secured together.

A fourth embodiment of an auto-injector (501) is shown in FIG. 32 and it includes a generally rectangular housing (503), cap (581) and body (571) from which the detent extends. The first part (503a) and the second part (503b) of the housing (503) are secured together by a snap fit. The manner of use and mode of action is similar to the third embodiment described above.

A fifth embodiment of an auto-injector (601) is shown in FIG. 33 and includes a generally rectangular housing (603) having a first part (603a) and a second part (603b). The injection end (607) of the housing (603) is provided with a complementarily shaped cap (781) and the handle end (605) is provided with a complementarily shaped lid (610) that is secured to the open handle end (605) in a snap fit.

In this embodiment the tip (615) is generally rectangular and includes a flat rear (617) that is arranged to be opposite the flat surface of a generally rectangular member (772) integrally formed with or attached at the trailing end (775) of the actuator (771). When pressure is applied to the tip (615) in use, the flat rear (617) of the tip (615) abuts the generally rectangular member (772) of the actuator (771) to push it in the direction of the handle end (605) of the auto-injector (601) and activate injection. The tip (615) acts directly on the actuator (771).

A generally rectangular body (671) is located in the handle end (605) of the housing (603). The body (671) has a bore (673) extending centrally therethrough in which the piston (611) is slideably secured. A detent (691) extends from the body and has six arms (693) that are circumferentially spaced about an annular member (696) that is intermediate the arms (693) and the body (671). The arms (693) extend axially and each terminates in an inclined tooth (695) on its inner surface. Each arm (693) includes a further radial flange (694) located between the annular member (696) and the teeth (695) that together with the teeth (695) are arranged to cooperatively engage a radially extending shoulder (720) of a collar (719) near the first end (715) on the plunger (611) prevent sliding movement of the collar internally of the arms and hold the plunger (611) in the loaded condition. A closure (685) is provided on the body and attached thereto by a snap fit of four deflecting arms (686) with teeth (688) into four apertures (690) centrally positioned on each side (692) of the generally rectangular body (671). With the closure (685) secured to it, the body (671) provides a snug fit in the handle end (605) of a part (603b) of the housing (603).

A compression spring (741) is received within the plunger (611) and is captured between an internal stop formation (not shown) on an internal surface within the plunger (611) and the closure (685) to provide a bias on the plunger in the direction of the detent (691). As explained with reference to the third embodiment, when the actuator is pushed towards the arms of the detent when pressure is applied to it via the tip, it slides internally of the arms to deflect the arms and release the collar from the teeth so that the compression spring can act on the plunger (611) to move it within the body (671).

Similar to previous embodiments, a syringe (751) is provided with a piston (157) slidable therein. The exposed end (759) of the piston (757) is releasably secured to the first end (715) of the plunger (611). When the plunger moves within the body under the force of the compression spring (741) it stops at a selected position relative to the housing when the needle has reached its selected depth of penetration for intramuscular injection. The plunger (611) then acts on the piston (757) to slideably move it in the barrel of the syringe and expel the drug therefrom (751).

Figure 34:
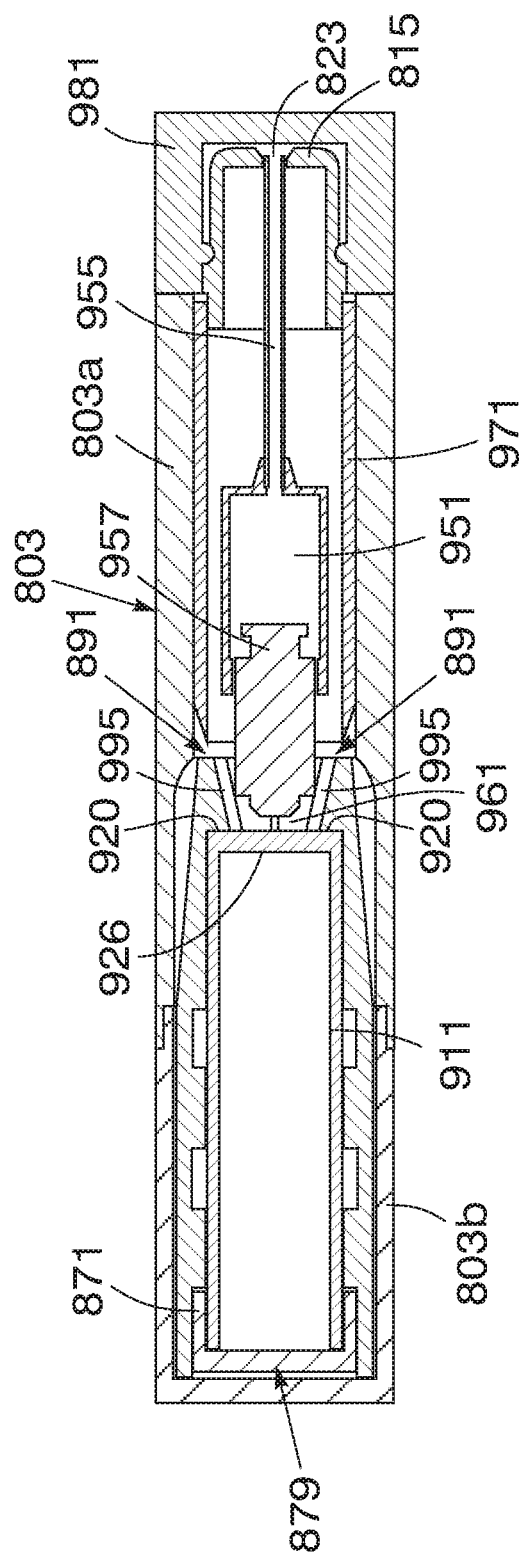
FIG. 34 is a sectional side elevation of a sixth embodiment of an auto-injector with the syringe in a stowed condition and the plunger in a loaded condition.

A sixth embodiment of an auto-injector (801) is shown in FIG. 34 and is a miniaturised version of the previously described embodiments with the relative spacing between some of the parts reduced. The auto-injector (801) includes a housing (803) and cap (981) that is rectangular in cross-section and has a first part (803a) and a second part (803b) secured together by a snap fit. In this embodiment, the teeth (995) of the detent (891) engage the shoulder (920) provided at the first end (915) of the plunger (911) to hold the plunger (911) in the loaded condition. The detent (891) is thus adjacent the lug (961) that is releasably secured to the piston (957), rather than acting on a neck portion or a collar of the piston near its end as in previous embodiments, thereby reducing the overall length of the auto-injector (801). The actuator (971) extends at least partially over the syringe (951) but not over the entire length of the needle (955). Additionally, the needle (955) terminates in the passage (823) in the tip (815) rather than being spaced therefrom resulting in a further reduction in overall length of the auto-injector as compared to previously described embodiments. The auto-injector (801) is a simplified version as compared to previous embodiments, as the body (871) does not include a separate closure but has a closed end (879)

providing an integral closure on the body. Furthermore, the compression spring (not shown) is captured between the closed end (879) and an internal surface (926) defined by the end (915) of the plunger, thereby leaving no free or unused space within the hollow plunger.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. An auto-injector which includes a housing having a handle end and an injection end and a tip extending from the injection end, with a syringe received in the housing and slidable between a stowed condition and an active condition, the syringe having a barrel with a piston movable therein and a needle extending therefrom, wherein the needle extends at least partially from the tip with the syringe in the active condition, and wherein the piston is releasably secured to one end of a plunger which is slidably secured within a body in the handle end of the housing and is operable through a bias provided by a motive source in the body to move from a loaded condition in which it retains the syringe in its stowed condition to a discharged condition under the bias provided by the motive source to move the syringe to the active condition and to slide the piston within the barrel to expel the contents of the syringe through the needle, the plunger being held in the loaded condition against the bias by a detent extending from the body and which can be selectively released by operation of an actuator which is slidably secured within the housing at least partially over the syringe, the actuator being operated by pressure applied to the tip in the direction of the handle end, wherein the housing is provided by two or more parts which are releasably secured together so that the syringe is replaceable, the two or more parts of the housing being configured to open up to provide access to a syringe, and in that the plunger is configured to be reset to the loaded condition when a new syringe is inserted into the body and wherein the bias provided by the motive source in the body is sufficient to provide intramuscular injection.

2. An auto-injector as claimed in claim 1 in which the motive source is a compressible element which is captured between a surface on the plunger and a closure on the body.

3. An auto-injector as claimed in claim 2 in which the closure provides a screw fit on the body.

4. An auto-injector as claimed in claim 3 in which the screw fit is configured to operably compress the compressible element when the closure is screwed onto the body.

5. An auto-injector as claimed in claim 1 in which the detent includes a plurality of outwardly resiliently flexible and circumferentially spaced arms, each arm having an inclined tooth at or near its end.

6. An auto-injector as claimed in claim 5 in which the inclined teeth provide a snap fit over a radially extending shoulder on the plunger.

7. An auto-injector as claimed in claim 5 in which the actuator is tubular with a tapered leading end configured to engage the detent internally of the inclined teeth and to displace the arms radially outwardly through axial movement towards the plunger.

8. An auto-injector as claimed in claim 7 in which an angle of inclination of the tapered leading end is selected to require a displacement of the actuator of between about 1 and 5 mm to displace the arms radially outwardly and release the inclined teeth from the detent.

9. An auto-injector as claimed in claim 8 in which the angle of inclination of the tapered leading end is selected to require the displacement of the actuator of between about 2 and 5 mm to displace the arms radially outwardly and release the inclined teeth from the detent.

10. An auto-injector as claimed in claim 1 in which the tip has a central passage through which the needle can move.

11. An auto-injector as claimed in claim 1 in which the tip is slidably secured within a circumferential groove in an injection end of the housing, the tip being biased toward an extended condition in which the tip substantially extends beyond the injection end of the housing by a second motive source provided in the circumferential groove.

12. An auto-injector as claimed in claim 1 in which a removable safety cap is provided on the housing over the tip.

13. An auto-injector as claimed in claim 1 in which a tubular spacer is provided internally of the housing between the tip and a trailing end of the actuator.

* * * * *